(12) United States Patent
Mirkov et al.

(10) Patent No.: US 11,806,522 B2
(45) Date of Patent: Nov. 7, 2023

(54) NEEDLE-ARRAY DEVICES AND RELATED METHODS

(71) Applicant: Cynosure, LLC, Westford, MA (US)

(72) Inventors: Mirko Georgiev Mirkov, Chelmsford, MA (US); James Boll, Auburndale, MA (US)

(73) Assignee: CYNOSURE, LLC, Westford, MA (US)

( * ) Notice: Subject to any disclaimer, the term of this patent is extended or adjusted under 35 U.S.C. 154(b) by 0 days.

(21) Appl. No.: 17/308,898

(22) Filed: May 5, 2021

(65) Prior Publication Data

US 2021/0346683 A1 Nov. 11, 2021

Related U.S. Application Data

(60) Provisional application No. 63/020,461, filed on May 5, 2020.

(51) Int. Cl.
*A61N 1/36* (2006.01)
*A61N 1/05* (2006.01)
*A61N 1/32* (2006.01)
*A61N 1/44* (2006.01)
(Continued)

(52) U.S. Cl.
CPC .......... *A61N 1/0502* (2013.01); *A61N 1/328* (2013.01); *A61N 1/36017* (2013.01); *A61N 1/36031* (2017.08); *A61N 1/44* (2013.01); *A61N 1/0476* (2013.01); *A61N 2001/083* (2013.01)

(58) Field of Classification Search
CPC .. A61N 1/0502; A61N 1/36031; A61N 1/328; A61N 1/36017; A61N 1/44; A61N 1/0476; A61N 2001/083; A61N 1/06; A61B 18/1477; A61B 2018/00458; A61B 2018/0047; A61B 2018/00476; A61B 2018/00875; A61B 2018/143
See application file for complete search history.

(56) References Cited

U.S. PATENT DOCUMENTS 7,618,429 B2 11/2009 Mulholland
9,095,357 B2 8/2015 Manstein
9,320,536 B2 4/2016 Na
(Continued)

FOREIGN PATENT DOCUMENTS

WO 2019/161038 A1 8/2019
WO WO-2019161038 A1 * 8/2019 ......... A61B 17/3203
(Continued)

OTHER PUBLICATIONS

PCT International Search Report and PCT Written Opinion for PCT International Patent Application No. PCT/US2021/030959; dated Aug. 24, 2021; (10 pages).

*Primary Examiner* — Ankit D Tejani
*Assistant Examiner* — Joshua Brendon Solomon
(74) *Attorney, Agent, or Firm* — K&L Gates LLP

(57) ABSTRACT

In part the disclosure relates to methods of treating acne, excessive sweating, unwanted hair, and/or unwanted blood vessels. The method may include providing a needle array comprising a plurality of needles; inserting plurality of needles into a dermis of a treatment area; detecting a location of an enlarged sebaceous gland; and energizing one or more of the plurality of needles to treat sebaceous glands, one or more sweat glands, vascular legions, unwanted hair follicles and/or unwanted blood vessels.

18 Claims, 23 Drawing Sheets

(51) Int. Cl.
*A61N 1/04* (2006.01)
*A61N 1/08* (2006.01)

(56) References Cited

U.S. PATENT DOCUMENTS

| | | |
|---|---|---|
| 9,480,836 B2 | 11/2016 | Na |
| 9,510,899 B2 | 12/2016 | Manstein |
| 9,775,774 B2 | 10/2017 | Na |
| 10,058,379 B2 | 8/2018 | Na |
| 10,799,285 B2 | 10/2020 | Mulholland |
| 10,869,812 B2 | 12/2020 | Na |
| 11,406,444 B2 | 8/2022 | Na |
| 2009/0326571 A1 | 12/2009 | Mulholland |
| 2010/0174223 A1* | 7/2010 | Sakamoto .......... A61K 41/0071 604/20 |
| 2010/0217253 A1* | 8/2010 | Mehta ................ A61B 18/1815 607/102 |
| 2020/0163578 A1* | 5/2020 | Aliverti ................ A61B 5/0538 |
| 2022/0008122 A1* | 1/2022 | Jauregui Johnston . A61B 90/04 |

FOREIGN PATENT DOCUMENTS

| | | | |
|---|---|---|---|
| WO | 2020/077019 A1 | 4/2020 | |
| WO | WO-2020077019 A1 * | 4/2020 | ......... A61B 18/1206 |
| WO | 2020/009351 A1 | 9/2020 | |

* cited by examiner

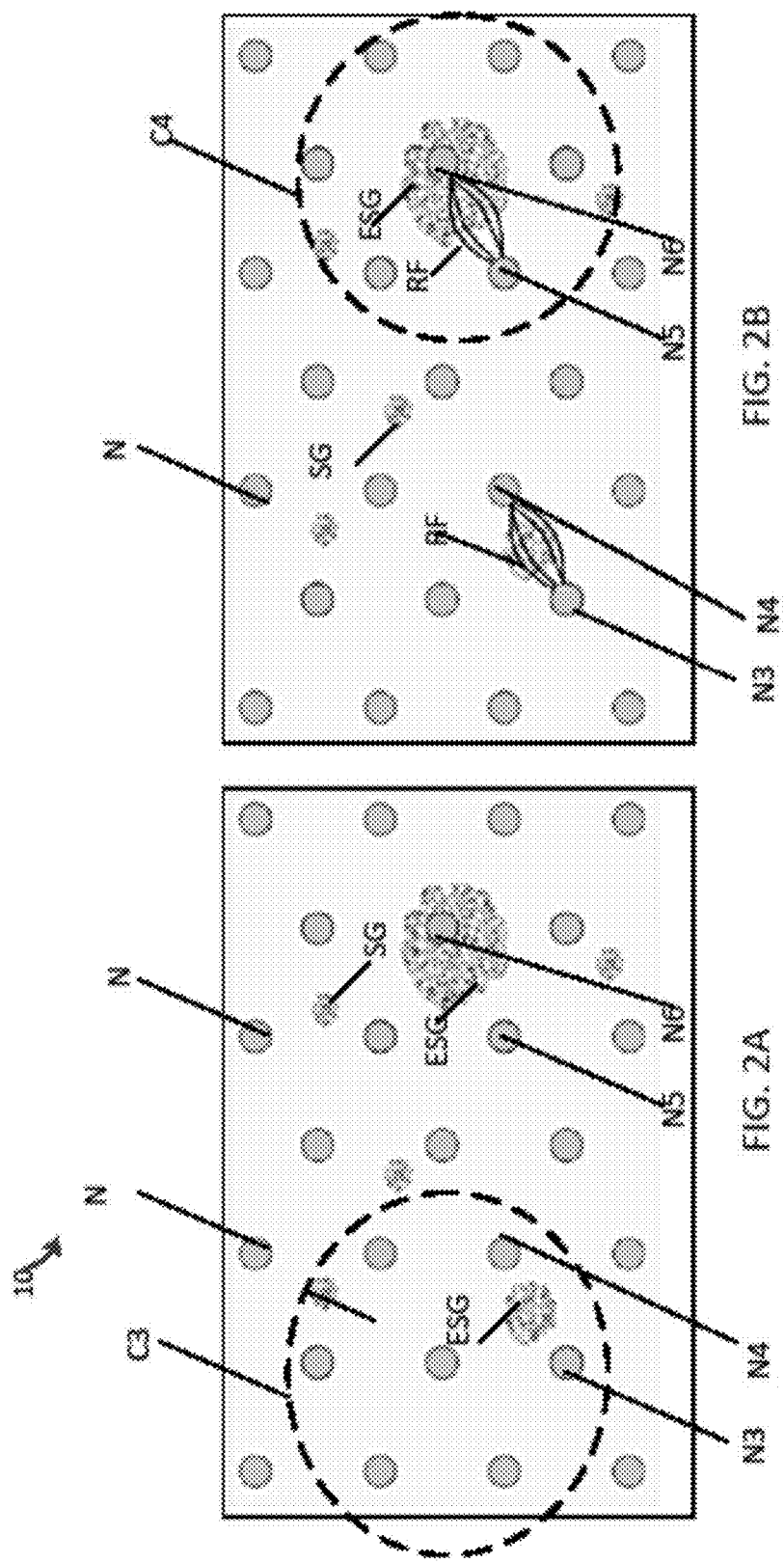

NEEDLE-ARRAY DEVICES AND RELATED METHODS

CROSS REFERENCE TO RELATED APPLICATIONS

This application claims priority to and the benefit of U.S. Provisional Patent Application No. 63/020,461 filed on May 5, 2020, the disclosure of which is herein incorporated by reference in its entirety.

BACKGROUND

The treatment of acne is of major concern to dermatologists. Acne accounts for millions of visits to dermatologists each year. Typically, acne arises in the early teen years and subsides by the mid-twenties. In many cases, particularly in women, acne remains a chronic problem well into the adult years.

Acne vulgaris, the most common form of acne, is the result of the secretion of sebum by the sebaceous gland into a blocked pore. Continued secretion results in buildup of the sebum in the blocked pore. Bacteria in the pore give rise to infection and a common unsightly skin condition known as pimples. Sebaceous gland hyperplasia is also a common form of acne in which the sebaceous gland grows or become enlarged as a result of overproduction of sebum.

In the past, physicians treated acne with radiation therapy to destroy the sebaceous gland. Radiation, however, does not specifically target the sebaceous glands, and can cause significant morbidity to normal tissue because of its mutagenic toxicity. Increased risk of cutaneous carcinoma has also been associated with radiation therapy. Many acne treatments do not eradicate the sebaceous glands selectively and without harm to surrounding normal tissue, and therefore remain non-curative and inadequate. The result is years of chronic therapy and potential scarring for the patient.

The present disclosure relates to systems and methods to address some or all of the foregoing and otherwise provide acne treatments and other cosmetic treatments using contact-based technologies.

SUMMARY

In part, the systems and methods discussed herein treat tissue in the human body. In a particular variation, systems and methods described below treat skin conditions that occur when hair follicles become plugged with oil and dead skin cells affecting various body parts, including the face, neck, and other areas traditionally prone to acne vulgaris.

Further, in part, the disclosure relates to systems and methods for identifying sebaceous glands in face and other tissue regions using tissue characterization circuitry and targeted treatment of sebaceous glands to treat or prevent acne using handheld applicator. In various embodiment, a microneedle array is used that includes groupings of needles arranged according to regular pattern such as hexagons or other regular polygons with needles arranged at vertices thereof and in the center or otherwise within the vertices. The needles can also be referred to as electrodes such that a microneedle array can be an array of electrodes.

In part, the disclosure relates to a method of treating acne. The method includes providing a needle array comprising a plurality of needles; inserting plurality of needles into a dermis of a treatment area; detecting a location of an enlarged sebaceous gland; and energizing one or more of the plurality of needles to treat the enlarged sebaceous gland.

In one embodiment, an enlarged sebaceous gland has diameter greater than about 50 µm. In one embodiment, detecting includes sending a low power pulse through each of the plurality of needles; collecting impedance data relative to each of the plurality of needles; and determining which of the plurality of needles is near the enlarged sebaceous gland based on the collected impedance data. In one embodiment, the low power pulse is a series of low power pulses that are iteratively sent until the collected impedance data shows contrast indicating the presence or absence of enlarged sebaceous glands.

In one embodiment, energizing includes sending energy through a needle of the plurality of needles located near the enlarged sebaceous gland. In one embodiment, one or more needles include liquid delivery ports and a channel to receive a solution. In one embodiment, the solution is a conductive solution.

In one embodiment, the method further includes addressing one or more needles of plurality of needles according to an energizing scheme such as a multiplexing sequence. In one embodiment, the plurality of needles is arranged in hexagonal clusters of needles wherein one needle is disposed within each such cluster. In one embodiment, the normally sized sebaceous glands are spared from targeted energy exposure.

In one embodiment, detecting a location of an enlarged sebaceous gland further includes performing an impedance mapping relative to treatment area. In one embodiment, detecting a location of an enlarged sebaceous gland further comprises identifying the enlarged sebaceous gland in response to one or more impedance measurements obtained during the impedance mapping. In one embodiment, detecting a location of an enlarged sebaceous gland further comprises measuring a difference in impedance between two adjacent needles spanning the sebaceous gland. In one embodiment, the method further includes performing a diagnostic impedance measurement relative to the treatment area. In one embodiment, the method further includes excluding high and/or low impedance values from the diagnostic measurement.

In part, the disclosure relates to a method of treating excessive sweating. The method includes providing a needle array comprising a plurality of needles; inserting the plurality of needles into a hypodermis of a treatment area; detecting a location of one or more sweat glands and energizing one or more of the plurality of needles to treat the one or more sweat glands In one embodiment, detecting includes sending a low power pulse through each of the plurality of needles; collecting impedance data relative to each of the plurality of needles; and determining which of the plurality of needles is near the one or more sweat glands based on the collected impedance data. In one embodiment, the low power pulse is a series of low power pulses that are iteratively sent until the collected impedance data shows contrast indicating the presence or absence of one or more sweat glands.

In one embodiment, energizing includes sending energy through a needle of the plurality of needles located near the one or more sweat glands. In one embodiment, one or more needles include liquid delivery ports and a channel to receive a solution. In one embodiment, the solution is a conductive solution.

In one embodiment, the method further includes addressing one or more needles of plurality of needles according to an energizing scheme such as a multiplexing sequence. In one embodiment, the plurality of needles is arranged in hexagonal clusters of needles wherein one needle is disposed within each such cluster. In one embodiment, a portion of the one or more sweat glands are spared from targeted energy exposure In one embodiment, detecting a location of one or more sweat glands further includes performing an impedance mapping relative to treatment area. In one embodiment, detecting a location of one or more sweat glands further comprises identifying the one or more sweat glands in response to one or more impedance measurements obtained during the impedance mapping. In one embodiment, detecting a location of one or more sweat glands further includes measuring a difference in impedance between two adjacent needles spanning the one or more sweat glands. In one embodiment, the method further includes performing a diagnostic impedance measurement relative to the treatment area. In one embodiment, the method further includes excluding high and/or low impedance values from the diagnostic measurement.

In part, the disclosure relates to a method of treating unwanted hair. The method includes providing a needle array comprising a plurality of needles; inserting the plurality of needles into a dermis of a treatment area containing unwanted hair; detecting a location of a hair shaft of an unwanted hair follicle and energizing one or more of the plurality of needles to treat the treat the unwanted hair follicle.

In one embodiment, detecting includes sending a low power pulse through each of the plurality of needles; collecting impedance data relative to each of the plurality of needles; and determining which of the plurality of needles is near an unwanted hair shaft based on the collected impedance data. In one embodiment, the low power pulse is a series of low power pulses that are iteratively sent until the collected impedance data shows contrast indicating the presence or absence of an unwanted hair shaft.

In one embodiment, energizing includes sending energy through a needle of the plurality of needles located near the unwanted hair follicle. In one embodiment, one or more needles include liquid delivery ports and a channel to receive a solution. In one embodiment, the solution is a conductive solution.

In one embodiment, the method further includes addressing one or more needles of plurality of needles according to an energizing scheme such as a multiplexing sequence. In one embodiment, the plurality of needles is arranged in hexagonal clusters of needles wherein one needle is disposed within each such cluster.

In one embodiment, detecting a location of unwanted hair further includes performing an impedance mapping of hair shafts of unwanted hair follicles. In one embodiment, detecting an unwanted hair further comprises identifying the unwanted hair shaft in response to one or more impedance measurements obtained during the impedance mapping. In one embodiment, detecting a location of an unwanted hair further comprises measuring a difference in impedance between two adjacent needles spanning the unwanted hair shaft. In one embodiment, the method further includes performing a diagnostic impedance measurement relative to the treatment area. In one embodiment, the method further includes excluding high and/or low impedance values from the diagnostic measurement.

In part, the disclosure relates to a method of treating vascular lesions. The method includes providing a needle array comprising a plurality of needles; inserting the plurality of needles into a dermis of a treatment area; detecting a location of one or more blood vessel (e.g., an unwanted blood vessel) and energizing one or more of the plurality of needles to treat the one or more blood vessel (e.g., the one or more unwanted blood vessel.

In one embodiment, detecting further includes sending a low energy power pulse through each of the plurality of needles; collecting impedance data relative to each of the plurality of needles; and determining which of the plurality of needles is near the one or more blood vessels based on the collected impedance data. In one embodiment, the low power pulse is a series of low power pulses that are iteratively sent until the collected impedance data shows contrast indicating the presence or absence of one or more blood vessels. In one embodiment, energizing includes sending energy through a needle of the plurality of needles located near the one or more blood vessels. In one embodiment, one or more needles comprise liquid delivery ports and a channel to receive a solution. In one embodiment, the solution is a conductive solution.

In one embodiment, the method further includes addressing one or more needles of plurality of needles according to an energizing scheme such as a multiplexing sequence. In one embodiment, the plurality of needles is arranged in hexagonal clusters of needles wherein one needle is disposed within each such cluster. In one embodiment, regions having one or more blood vessels with normal blood concentrations are spared from targeted energy exposure. In one embodiment, detecting a location of one or more blood vessels further includes performing an impedance mapping relative to treatment area. In one embodiment, detecting a location of one or more blood vessels further comprises identifying one or more enlarged blood vessels in response to one or more impedance measurements obtained during the impedance mapping.

In one embodiment, detecting a location of one or more blood vessels further comprises identifying one or more elevated blood volume fraction in response to one or more impedance measurements obtained during the impedance mapping. In one embodiment, detecting a location of one or more blood vessels further includes measuring a difference in impedance between two adjacent needles spanning the one or more blood vessels. In one embodiment, detecting a location of one or more regions of elevated blood volume fraction further comprises measuring a difference in impedance between two adjacent needles spanning the one or more regions of elevated blood volume fraction. In one embodiment, the method further includes performing a diagnostic impedance measurement relative to the treatment area. In one embodiment, the method further includes excluding high and/or low impedance values from the diagnostic measurement. In some embodiments, certain blood vessels are detected via impedance mapping, but are intentionally untreated whereas other of the detected blood vessels are treated via RF power by energizing one or more of the plurality of needles, because the treated blood vessel(s) are expected or understood to be the visible vascular lesion(s) and once the certain blood vessel(s) are treated the cosmetic appearance of the vascular lesion(s) are expected to improve.

In part, the disclosure relates to a method of treating tissue. The method includes providing a needle array comprising a plurality of needles; inserting plurality of needles into on one or more tissue layers of a treatment area; detecting a location of a tissue target; and energizing one or more of the plurality of needles to cosmetically treat one or more portions of a tissue target.

In one embodiment, the tissue target is selected from group that includes one or more of a hair follicle; a sweat gland, blood vessel, a vascular lesion and a sebaceous gland.

In one embodiment, detecting a location of a tissue target further includes sending a low power pulse through each of the plurality of needles; collecting impedance data relative to each of the plurality of needles; and determining which of the plurality of needles is near the tissue target based on the collected impedance data. In one embodiment, detecting a location of a tissue target further includes performing an impedance mapping relative to treatment area.

Although, the disclosure relates to different aspects and embodiments, it is understood that the different aspects and embodiments disclosed herein can be integrated, combined, or used together as a combination system, or in part, as separate components, devices, and systems, as appropriate. Thus, each embodiment disclosed herein can be incorporated in each of the aspects to varying degrees as appropriate for a given implementation. Further, the various systems, probes, applicators, needle arrays, controllers, components and parts of the foregoing can be used with any suitable tissue surface, cosmetic and aesthetic applications, and medical applications and other methods and conjunction with other devices and systems without limitation.

These and other features of the applicant's teachings are set forth herein.

BRIEF DESCRIPTION OF THE FIGURES

FIGS. 2A and 2B are schematic diagrams showing application of a needle array to tissue for identifying and treating certain classes of tissue or organ structures such as enlarged sebaceous glands according to an illustrative embodiment of the disclosure.

DETAILED DESCRIPTION

Figure 1A:
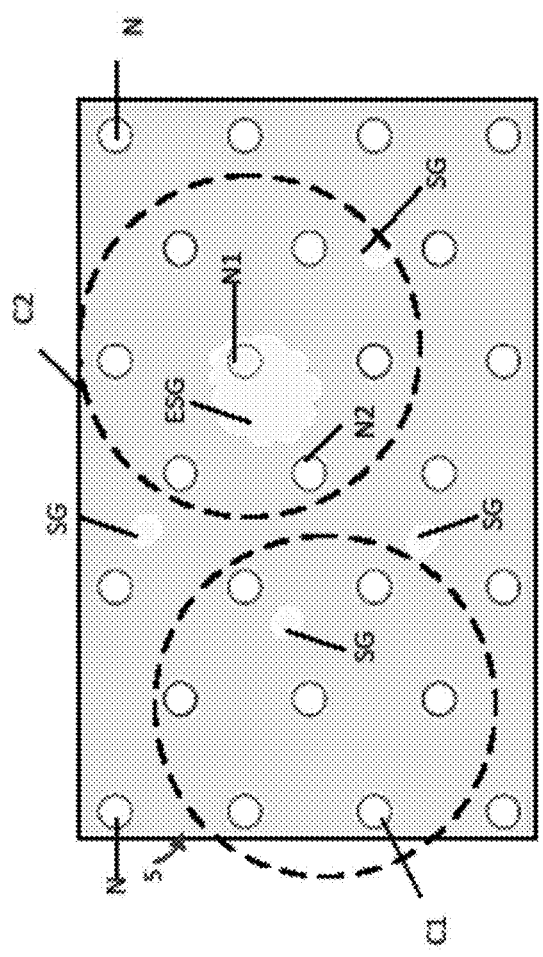
FIGS. 1A and 1B are schematic diagrams showing application of a needle array to tissue for identifying and treating certain classes of tissue or organ structures such as enlarged sebaceous glands according to an illustrative embodiment of the disclosure.

Techniques are disclosed that describe a device and method for energy delivery to sebaceous glands for treatment of acne and/or for detecting certain types of sebaceous glands for treatment. Sebaceous glands are located within the dermis of the skin. Sebaceous glands are distributed over the entire body with the exception of the palms of the hands and the soles of the feet; they are most abundant on the scalp and face. Sebaceous glands function by producing and releasing a lipid substance, sebum, in order to help protect and lubricate the surface of the skin. Sebum is composed of lipids, cellular debris, and keratin. Acne is generally associated with enlarged sebaceous glands, which occurs, for example, when the outlet from the sebaceous gland to the surface of the skin is, plugged allowing sebum to accumulate in the follicle and this results in the enlarged sebaceous glands. RF energy is directed to a treatment device that includes a needle array in which needles are operable to transmit RF treatment energy to tissue and specifically to features within tissue, such as enlarged sebaceous glands for treatment. Sebaceous glands help maintain moisture and lubrication of the skin and hair. Further, some research suggests sebaceous glands also contribute to the operation of the immune system as well. Accordingly, it is important for any acne treatment focused on treating enlarged sebaceous glands that the treatment, also spare normal sebaceous glands that provide or support important functions for the skin and potentially the immune system.

In one embodiment, treatment is performed across a tissue region for example, between a pair of needle electrodes. The array may be integrated in one or more handpieces or applicators. In some embodiments, an array is a detachable consumable such as, for example, a detachable needle array.

Suitable microneedling systems may have a power delivery level that ranges from about 1 milliwatt to about 10 kilowatts, or from about 100 milliwatts to 100 watts. Such microneedling systems may deliver RF energy for a period of from about 1 ns to about 10 seconds, or from about 1 microsecond to about 1 second, or from about 1 millisecond to about 500 milliseconds.

Suitable microneedling systems include microneedling electrodes that are also referred to as needle electrodes and/or electrodes and these may be non-insulated, insulated or substantially insulated such that only the tip of the needle is non-insulated such that RF energy may be delivered at the targeted depth of the tip in the tissue. The targeted depth of the needle electrodes may vary based on the target tissue, for example, sebaceous glands are at a depth of from about 1 to 2 mm from the skin surface and sweat glands are at a depth that is below the dermal/hypodermal junction that can range from about 2 to about 5 mm depth from the skin surface. Each of the needle electrodes can have a diameter that ranges from about 100 to about 1000 micrometers, more preferably from about 200 to about 600 micrometers. The desire for a relatively small diameter needle to avoid the pinch/pain of entry into the skin surface must be balanced against the need for the electrode to remain straight/non bended during repeated use. Future material advances could yield even smaller diameter electrodes that meet this need.

In various embodiments, treatment is applied over a few treatment sessions to reduce size of, to damage, and/or to destroy one or more enlarged sebaceous glands. In turn, the size reduction, damage, or destruction of such glands and/or exposure to RF energy reduces the symptoms of acne vulgaris or sebaceous glands hyperplasia. Further, in various embodiments, RF energy is applied in a controlled amount and/or pursuant to a time varying pattern such as a multiplexed delivery through various clusters of needles to interfere with sebaceous gland production of sebum. Over a few treatment sessions the enlarged sebaceous glands can be regulated or controlled or otherwise modified relative to their pre-treatment state to reduce or cease sebum production. In some embodiments, after an initial treatment regimen occasional treatments may be applied to prevent, mitigate, or otherwise change incidents and/or outbreaks of acne.

Typically, sebum provides moisturizing and lubrication compounds to the skin and possibly plays a role in the skin immune barrier. However, in some situations, sebum is excessively produced by one or more enlarged sebaceous glands. Without being held to a particular theory or mechanism, acne vulgaris appears to result in response to variations (e.g., increasing) in secretion of sebum by the sebaceous glands and the flow of sebum to the skin surface. Generally, increased sebum production in the sebaceous glands and/or restriction or blockage of the flow of sebum lead to the typical symptoms of acne vulgaris or sebaceous glands hyperplasia.

Other energy-based treatments for acne vulgaris involve devices that deliver energy to an affected area. However, typically, these devices cannot identify the location of the sebaceous glands in the dermis without a secondary device. Generally, various separate imaging technologies can be used to identify locations of the sebaceous glands, such imaging technologies include confocal microscopy, optical coherence tomography, multiphoton microscopy and other similar techniques that take into account the scattering properties of the human dermis. Typically, these imaging technologies are used with a subsequent targeted energy delivery that spares most of the epidermis and dermis and damages the sebaceous glands with minimal surrounding tissue damage. These methods can be combined with one or more embodiments disclosed herein and benefit from the synergies with the needle arrays and treatment modes disclosed herein.

Figure 1B:
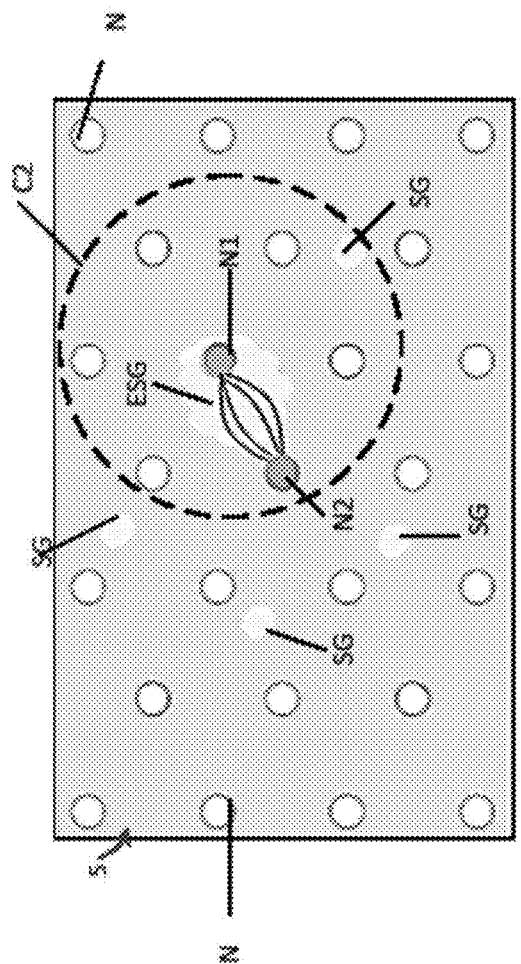

In various embodiments, this disclosure describes methods and systems for detecting and targeting sebaceous glands and subsequently directing and delivering RF energy configured to treat the sebaceous glands within the targeted regions. In various embodiments, an RF energy diagnostic and delivery device includes an array of electrodes also referred to as needles or microneedles. FIGS. 1A and 1B are schematic diagrams showing application of a needle array 5 (also referred to as a microneedle array or an array of electrodes) to tissue for identifying and treating certain classes of tissue or organ structures such as enlarged sebaceous glands. As shown, in FIGS. 1A and 1B, an array of needles with individual needles N, generally, are shown. Each needle N is in electrical communication with a control system and an energy delivery system. Each needle is an electrode in various embodiments. In various embodiments, RF energy can be generated pairwise between at least one pair of two needles or between at least one needle and a neutral electrode pad attached to the patient's body.

With the overall needle array 5, there are clusters or one or more subarrays of needles that can be arranged in various patterns. These needles are in contact with tissue that includes sebaceous glands SG and an enlarged sebaceous gland ESG. A normal sebaceous gland SG has a diameter that measures less than or equal to about 50 µm. An enlarged sebaceous gland ESG has a diameter that measures greater than 100 µm, for example, between 100 µm and 1 mm, or for example, between 100 µm and 5 mm. In FIG. 1A, clusters C1 and C2 and in FIG. 1B cluster C2 are shown as individual hexagonal clusters or subarrays. Six needles are disposed at the vertices and one needle is disposed in the center. In cluster C2, needles N1 and N2 are shown relative to an enlarged sebaceous gland ESG. FIGS. 2A and 2B also show a needle array 10 with various needles N and hexagonal clusters C3 and C4.

The selection of a hexagonal arrangement of needle clusters offers an advantage for an ordered arrangement with the largest number of equidistant nearest neighbors, in this case six, for any electrode. Sebaceous glands in the skin can be located by using a needle array that includes a hexagonal cluster or arrangement of electrodes or needles such as microneedles. Dermis and sebum, a lipid, have differing impedances, the impedance of dermis is similar to the impedance of wet skin and the impedance of sebum is similar to the impedance of fat tissue. As a result, a diagnostic scan of the needle grid locates the pairs of adjacent needles with large sebum concentration in the space between them (enlarged sebaceous glands). For example, in FIGS. 1A and 2A a scanning process is used to distinguish SGs from ESGs. In turn, ESGs are treated with RF as shown in FIGS. 1B and 2B. In FIG. 2B, two ESGs are treated simultaneously.

When normal sebaceous glands are scanned, such as those having a diameter less than or equal to about 50 µm, the resulting impedance measurement, as a difference between two adjacent needles spanning the sebaceous gland, will be the lowest impedance difference or otherwise trend within a range of lower impedance difference characteristic of normal, i.e., not enlarged, sebaceous glands, or no sebaceous glands in the scanned region. The edge-to-edge separation between the microneedles in the array can vary between about 100 µm and about 3 mm, or from about 100 µm and about 1 mm or from about 200 µm and about 500 µm.

Larger sebaceous glands (e.g., ESGs) show a greater impedance variation in comparison to a baseline measurement. Smaller sebaceous glands (SGs) will show lower impedance variation in comparison to baseline. Baseline may be defined as the average impedance measured by groups of electrodes when the outliers (e.g., high or low impedance) are excluded. For a given treatment session, the microneedling array is inserted into a tissue area. The array may be releasably or directly coupled to a reusable or disposable handpiece. A diagnostic scan of the tissue area is accomplished such the impedance of each electrode or alternatively the impedance between each pair of electrodes is measured. The high and/or low impedance values from this diagnostic measurement are excluded and a baseline impedance is established for this specific tissue area. In one embodiment, when an impedance value is determined to be high and/or low then the microneedle or the pair of microneedles associated with that high and/or low value is earmarked for subsequent therapeutic treatment. In another embodiment, once the baseline impedance is determined, the system will subsequently revisit the high and/or low impedance values and determine which ones to interrogate for therapeutic purposes based, for example, on the underlying frequency of the system.

The edge-to-edge separation between the microneedles in the array can vary between about 100 µm and about 1 mm, between about 200 µm and about 500 µm. For example, in FIG. 3, we expect that based on the contrast that we see in the impedance amplitude ratio from about 0.01 MHz to about 1000 MHz, and from about 0.03 MHz to about 500 MHz, and between about 1 MHz to about 10 MHz it will be possible to design diagnostic systems that discerns the presence or absence of enlarged sebaceous glands, ESGs.

In other embodiments, the array may be configured in shapes other than hexagonal, such other shapes, include, but are not limited to, rectangular, pentagonal, octagonal, circular, or other geometries. The array of electrodes or microneedles is inserted in the treatment area of the skin immediately prior to treatment. Each array 5, 10 shown in FIGS. 1A and 1B, and 2A and 2B is shown in contact with tissue for a treatment session.

In various embodiments, once an array of electrodes (e.g., a needle array or a microneedle array) is properly placed, treatment of an affected sebaceous glands is a two-step process. First, in at least one example, low energy diagnostic pulses are applied to the needle array. Each sebaceous gland is located based on the difference of the dielectric properties of sebum versus skin dermis. A control system causes the needle array to be energized with either a monopolar or a bipolar scheme. In a monopolar diagnostic step, the impedance between each electrode in the needle array and the neutral return electrode is used to identify the electrodes that have been inserted into a sebaceous gland. In some instances, a needle from the needle array can, by chance, be inserted within a sebaceous gland. In a bipolar diagnostic step, the measured impedance between pairs or groups of two, three, or more electrodes is used to calculate the location of sebaceous glands that are located between electrodes of the array. In various embodiments, the control system sequentially energizes each available group of two, three, or more electrodes to map each of the sebaceous glands in the treatment region defined by the needles in the needle array.

The diagnostic step concludes with the identification of a subset of electrodes in the needle array that have been inserted directly in a sebaceous gland (by chance) and the nearest pair (or larger group of electrodes) that surround other sebaceous glands. In various embodiments, the use of impedance variation determines the location of the sebaceous glands and their approximate size. Larger sebaceous glands create a larger impedance variation when surrounded by groups of two or more electrodes when compared to the needle array average impedance measured between similar groups of electrodes in the absence of sebaceous glands.

In one embodiment, a selected subset of pairs of adjacent needles, such as N1 and N2 in FIGS. 1A and 1B or the pairs of needles N3 and N4 and N5 and N6 in FIGS. 2A and 2B are energized to treat the enlarged sebaceous gland, ESG, with RF energy. These pairs may be selected based on the ESGs with the highest lipid concentration determined in the diagnostic step and are then treated using a treatment methodology. Specifically, these needle pairs may be energized for a time interval approximately equal to the thermal relaxation time of the tissue between each respective needle pairs as shown in FIGS. 1B and 2B, wherein RF is being delivered to initiate selective RF heating. For some treatment sessions, selective RF heating will require high power for a short time.

In one embodiment, the array is selectively energized to manage or alleviate pain. Simultaneously energizing the selected subset of needles for a short time interval may alleviate the associated pain. Application of shorter pulses at therapeutic level is sometimes perceived as less painful than longer pulses delivering the same energy. Alternatively, the array is selectively energized to manage or alleviate pain by treating only one or a few ESGs at a time. Cooling and other techniques may also be used. In various embodiments, the needle array is implemented as a handpiece or an applicator that can be used with one or more umbilicals or combination treatment systems. Epidermal cooling can be provided to manage pain by distracting the patient.

Impedance variation, in various embodiments, provides a way to estimate size of the located sebaceous glands. Generally, a non-inflamed sebaceous glands are about 50 μm in diameter or less. However, in various instances when a sebaceous gland's output gets obstructed, the gland grows in size, potentially becomes inflamed and can have a diameter of a millimeter or more. Larger sebaceous glands show a greater impedance variation in comparison to baseline. Smaller glands will show lower impedance variation in comparison to baseline. Baseline may be defined as the average impedance measured by groups of electrodes when the outliers (e.g., high or low impedance) are excluded. In various embodiments, the controller system selects the most enlarged sebaceous glands ESG for energy delivery. The cut off can be defined as ESG that are treated may be 50% larger, 2 times larger, 3 times larger, 4 times larger, or 5 times larger than the normally sized SG. Normally sized, and smaller sized, sebaceous glands lead to a smaller impedance contrast and can be left intact. A round robin treatment scheme from largest to smaller ESG may be chosen based on available RF power and pain sensation. Alternatively, all ESGs may be treated by a single short pulse. In any case, the control system chooses the ESGs to be treated so that each of the treatment regions is surrounded by untreated regions.

In various embodiments, a diagnostic step can be performed at frequencies where the sebaceous glands have large dynamic change of their specific impedance when heated. For example, in one embodiment, the diagnostic step starts with a frequency corresponding to a specific impedance difference between the sebaceous glands and the epidermis of approximately two times and larger. Then the diagnostic proceeds in two stages. In the first stage an intermediate power diagnostic pulse is applied between the diagnostic electrode groups. The intermediate power of the diagnostic pulse is chosen so that it produces the desired dynamic change in the specific impedance without undesirable heating effects for example dermal coagulation is avoided. The intermediate diagnostic power is chosen so that it leads to much larger specific impedance change in the sebaceous glands due to the intermediate power RF heating than in the surrounding dermis. In the second stage (possibly performed in parallel with the first stage) the impedance localization is based on the observed dynamic change in the impedance of the sebaceous glands due to the intermediate power RF heating vs much smaller change in the dermal impedance. Diagnostic power levels may vary between about 1 nano Watt and about 10 Watts. Preferred power levels will be determined for an exemplary assembly and will be based on actual tissue testing including parasitic impedance of the exemplary assembly.

Figure 3:
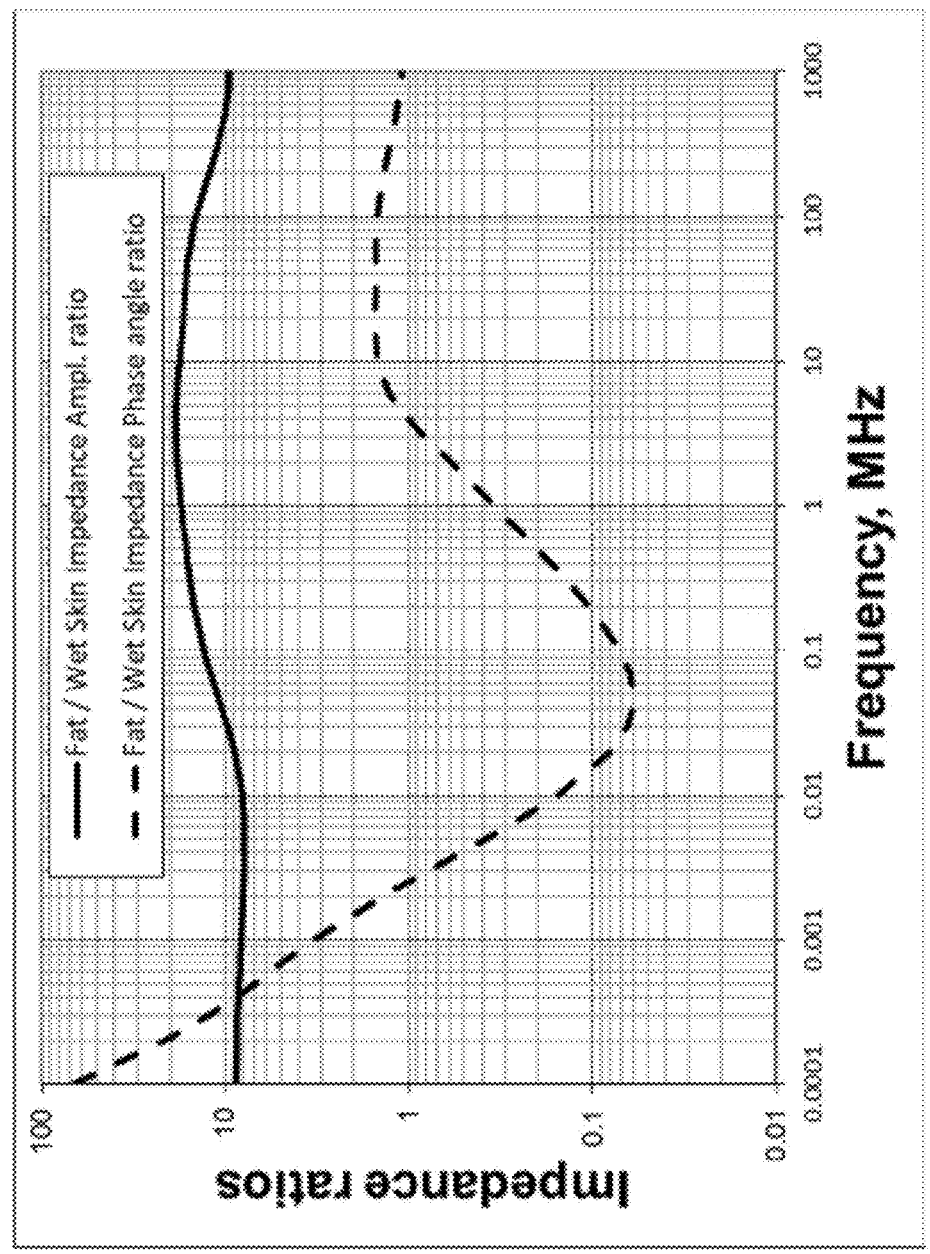
FIG. 3 is a plot showing ratios of the impedance properties of fat vs wet skin, specifically, the ratio of fat impedance amplitude to wet skin impedance amplitude (in solid line) and the ratio of fat impedance phase angle to wet skin impedance phase angle (in broken line) over a frequency range from about 0.0001 MHz to about 1000 MHz (e.g., about 100 Hz to about 1 GHz) according to an illustrative embodiment of the disclosure.

In another embodiment, the diagnostic step can be performed by sweeping the diagnostic frequency over a range where the specific impedance of the sebaceous glands and/or dermis and/or their ratio changes rapidly as the diagnostic frequency changes. This diagnostic method may be particularly beneficial when parasitic impedance of the diagnostic system including the electrodes generates data with a low signal to noise ratio. For example, based on the specific impedance phase angle ratio, i.e., the ratio of fat impedance amplitude to wet skin impedance phase angle (in dashed line), plotted as shown in FIG. 3, the frequency range between about 1 kHz and about 1 MHz offers a range of rapidly changing specific impedance phase angle ratio. In various embodiments, when determining the location of a sebaceous gland, here fat is a surrogate for sebaceous gland tissue and wet skin is a surrogate for dermal tissue, an optimal frequency allows for contrast between the specific impedance of the sebaceous gland and the surrounding dermis.

In various embodiments, after a target sebaceous gland is located, a controller system directs higher power treatment pulses, pulses suited to treatment rather than detection/diagnosis, to each electrode that is identified to be inside a target sebaceous gland (e.g., an enlarged sebaceous gland) or in close proximity to the target sebaceous gland (e.g., an enlarged sebaceous gland). In most instances, only a relatively small fraction of the electrodes of the needle array will be in the proximity of the targeted sebaceous gland causing only a small portion of the dermis in the vicinity of the targeted sebaceous gland to be thermally damaged.

In various embodiments, RF power levels during a treatment session may vary between about 0.001 Watts and about 1000 Watts. Preferred power levels will be determined for an exemplary assembly and will be based on actual tissue testing including parasitic impedance of the exemplary assembly. For example, the preferred treatment power levels for an exemplary assembly may be determined by examining a group of skin histology sections with treatments corresponding to differing power levels. In turn, the corresponding disruption to the enlarged sebaceous glands may be evaluated in each of the histology sections. This evaluation may also include verifying that the normally sized sebaceous glands are not damaged. The associated power levels that are correlated with histology sections having disrupted/damaged large sebaceous glands and undamaged normally sized glands may be used to set the power levels for a given treatment session.

In some embodiments, the fractional energy delivered to the dermis causes additional benefits, such as collagen remodeling and skin tightening. In various embodiments, the control system prioritizes the electrodes with the largest impedance differential to be energized so that the thermally damaged tissue fraction heals without undesirable side effects. The control system may choose the ESGs to be treated so that each of the treatment regions is surrounded by untreated regions. Such non-uniform or adaptive "fractional" treatment speeds up tissue healing.

In various embodiments, in an optimal situation, a frequency for treatment can be chosen so that the impedance of the targeted sebaceous glands is lower than the surrounding dermis. In this case, the sebaceous glands are more efficiently heated and reach a higher temperature than the surrounding dermis, for example, the targeted sebaceous glands temperature is envisioned to be higher than about 45° C. during the treatment.

In other embodiments, the treatment frequency can be chosen so that the impedance of the sebaceous glands is similar or higher than the surrounding dermis. In this situation, the sebaceous glands may still be heated to a higher temperature than the surrounding dermis because of their lower heat capacity and lower heat conductivity. Alternatively, the treatment frequency can be chosen so that the impedance of the sebaceous glands is similar or higher than the surrounding dermis. In that case the sebaceous glands will be heated by heat diffusion from the surrounding dermis that will be heated more efficiently. Limiting the thermal damage in the dermis only to regions containing ESGs between RF electrodes in a fractionated arrangement allows the thermally damaged dermal regions to heal quickly after the treatment. For the available range of frequency data for fat and wet skin, from about 100 Hz to about 1 GHz, the fat impedance is higher than the wet skin impedance and that corresponds to more efficient heat generation in the dermis and heating of the sebaceous glands by heat diffusion from the surrounding dermis.

When the RF frequency is chosen so that the ESGs are heated more efficiently than the dermis, the energized period of time corresponds to the thermal relaxation time of the sebaceous tissue. When the RF frequency is chosen so that the dermis is heated more efficiently than the ESGs, the energized period of time corresponds to the thermal relaxation time of the dermal tissues and the embedded ESGs between the RF electrodes. Additionally, the period of time when the RF electrode groups are energized can be chosen such that the enlarged sebaceous glands accumulate heat and increase their temperature higher than the normal much smaller diameter sebaceous glands. In various embodiments, this treatment of a sebaceous gland is called selective electrothermolysis.

An alternative method for treatment of the sebaceous glands can be based on selective heating and coagulation of the blood vessels feeding the glands.

In a first diagnostic step the locations of the enlarged sebaceous glands are determined as outlined above. In the second treatment step the higher energy treatment pulses are delivered first only to the electrodes that are identified to be inside sebaceous glands. Then the electrodes identified to be in close proximity to sebaceous glands are used to deliver higher energy treatment pulses that will heat selectively, and coagulate all or a portion of the blood vessels in the proximity of the sebaceous glands. The objective is to reduce and or remove the blood supply feeding the sebaceous gland.

Figure 4:
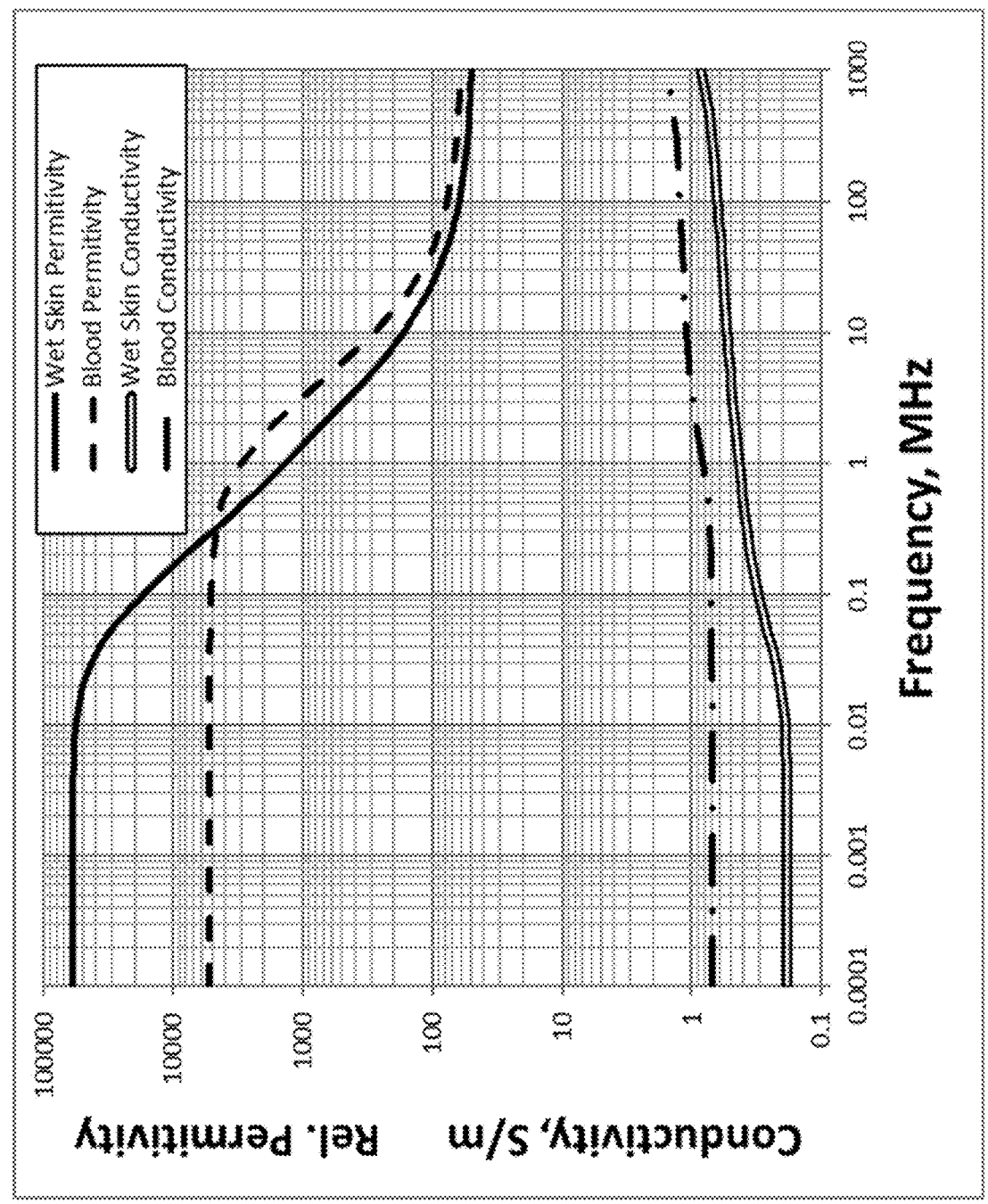
FIG. 4 is a plot showing permittivity and conductivity of blood vs wet skin (as a surrogate for dermal tissue) as four different curves over a frequency range from about 0.0001 MHz to about 1000 MHz (e.g., 100 Hz to 1 GHz) according to an illustrative embodiment of the disclosure.

The dielectric properties of wet skin, or dermis, and blood are plotted on FIG. 4, based on data from Gabriel et al., "*The dielectric properties of biological tissues: I Literature survey, Phys. Med. Biol.* 41 (1996) 2231-2249, and Gabriel S, Lau R W, Gabriel C. "*The dielectric properties of biological tissues: III. Parametric models for the dielectric spectrum of tissues*". Physics in Medicine & Biology. 1996 November; 41(11):2271 and Gabriel C, Peyman A, Grant E H. *Electrical conductivity of tissue at frequencies below* 1 *MHz Physics in medicine & biology.* 2009 Jul. 27; 54(16):4863. The calculated specific electrical impedance amplitude |z| and phase angle θ for wet skin and blood are plotted on FIGS. 5 and 6 for frequencies between 100 Hz and 1 GHz. The ratios of the specific electrical impedance amplitude and phase angle of blood vs dermis are plotted on FIG. 7. FIG. 7 indicates that there are extensive frequency ranges where the specific impedance of blood and dermis differs by a factor of more than 2. For example, for frequencies between about 100 Hz and about 50 MHz, the blood specific impedance is between about 25% and about 50% of the dermis impedance. Delivery of RF power in the range of between about 100 Hz and about 50 MHz through the electrodes identified to be in close proximity to targeted sebaceous gland will lead to selective power delivery to the blood vessels with up to 2 to 4 times lower power density delivered in the surrounding dermis (i.e., in the dermis surrounding the blood vessels).

The lower RF impedance of the blood in the blood vessels will lead to higher RF power delivered through the blood vessels located between the two, or more, electrodes that are identified near a targeted sebaceous gland. RF power flow through blood vessels and the associated blood vessel heating will lead to injury of the blood vessels walls. The RF pulse on-time is preferentially selected to cause selective heating of the vessel based on the theory of selective photo-thermolysis, R. Rox Anderson et al., "*Selective Photothermolysis: Precise Microsurgery by Selective Absorption of Pulsed Radiation, Science*", Vol. 220 pp. 524-528. applied to the selective blood vessel heating by RF power. Higher frequency RF power delivery would be preferable due to the "skin effect" of larger current density in the periphery of an RF conductor and more localized injury to the blood vessel wall. Thermal, mechanical and other injury to the blood vessels walls will lead to coagulation of all or a portion of the blood in the injured vessel within 5 to 100 seconds after the delivery of the RF power, Falati et al., "*Real-time in vivo imaging of platelets, tissue factor and fibrin during arterial thrombus formation in the mouse*", *Nature Medicine•*Volume 8•Number 10•October 2002, pp. 1175-1180 and Furie et al., "*Thrombus Formation in Vivo*", *The Journal of Clinical Investigation*, Vol. 115:12, December 2005, pp. 3355-3362. Coagulation as described here can include the start of the cascade of events that lead to full coagulation of the blood vessel. Coagulation of the blood vessels supplying the sebaceous gland will lead to gland disruption until angiogenesis reestablishes blood delivery to the gland. The disruption of the blood flow to the gland may lead to decrease in the size of the sebaceous gland. The gland disruption may lead also to gland necrosis. Decrease in size or necrosis of enlarged sebaceous glands in a skin area will lead to degrease in the acne symptoms in that area.

In various embodiments, when an RF electrode is energized, areas closer to the RF electrode may reach undesirable temperatures due to the higher current density. In one example, undesirable electrode temperatures can be alleviated and/or mitigated by making the delivery needle electrodes hollow so that cold conductive liquid (e.g., saline) can be delivered immediately prior to energy delivery.

Devices and Apparatus for RF Delivery

Figure 8:
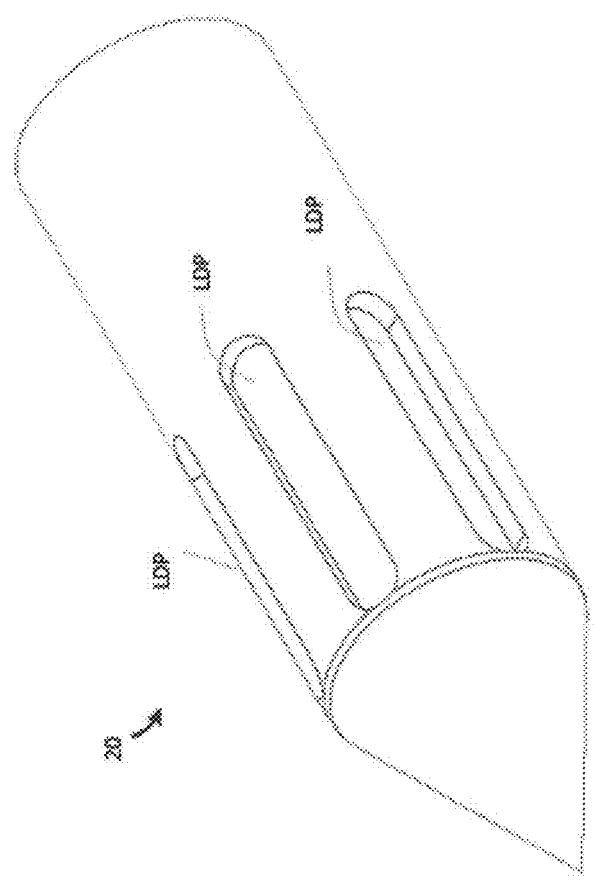
FIG. 8 is a schematic diagram of an exemplary RF electrode needle with liquid delivery ports around its periphery according to an illustrative embodiment of the disclosure.
Figure 9:
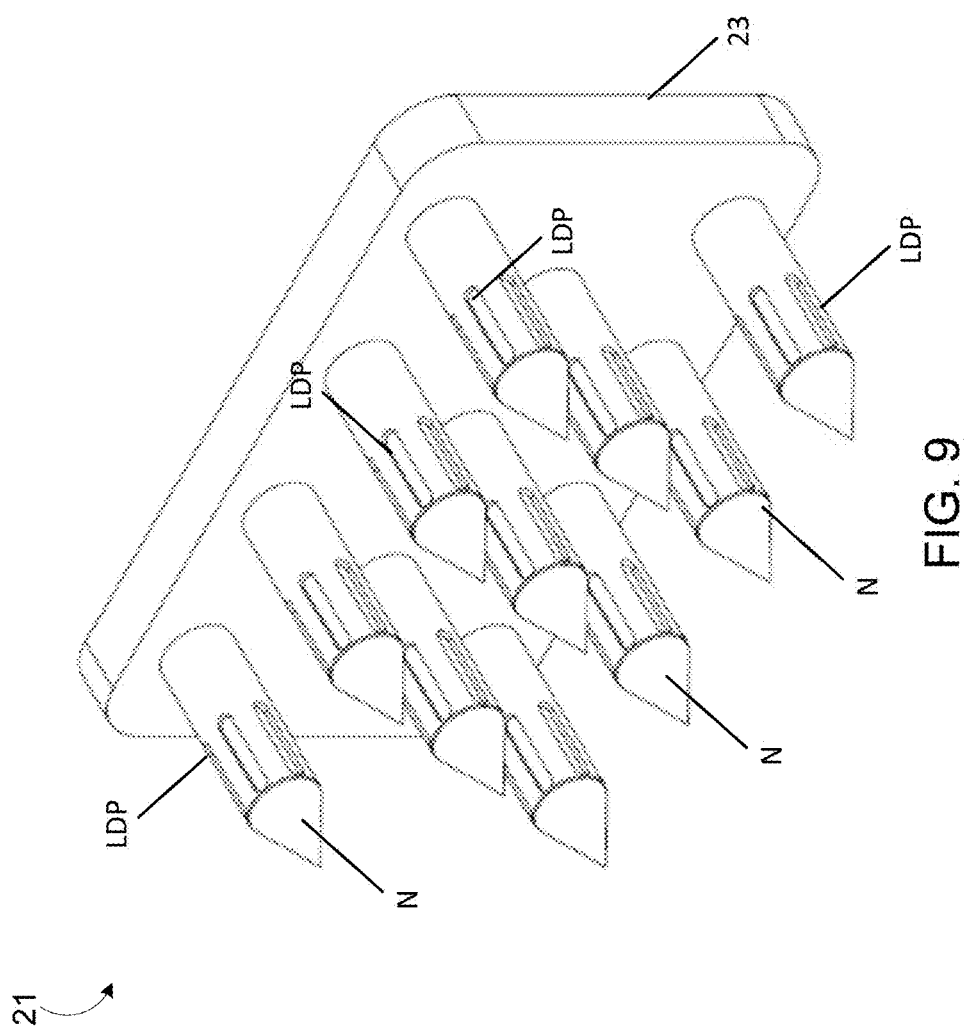
FIG. 9 is a schematic diagram of exemplary RF electrode needles with liquid delivery ports mounted on an electrode applicator holder in a hexagonal pattern according to an illustrative embodiment of the disclosure.
Figure 10:
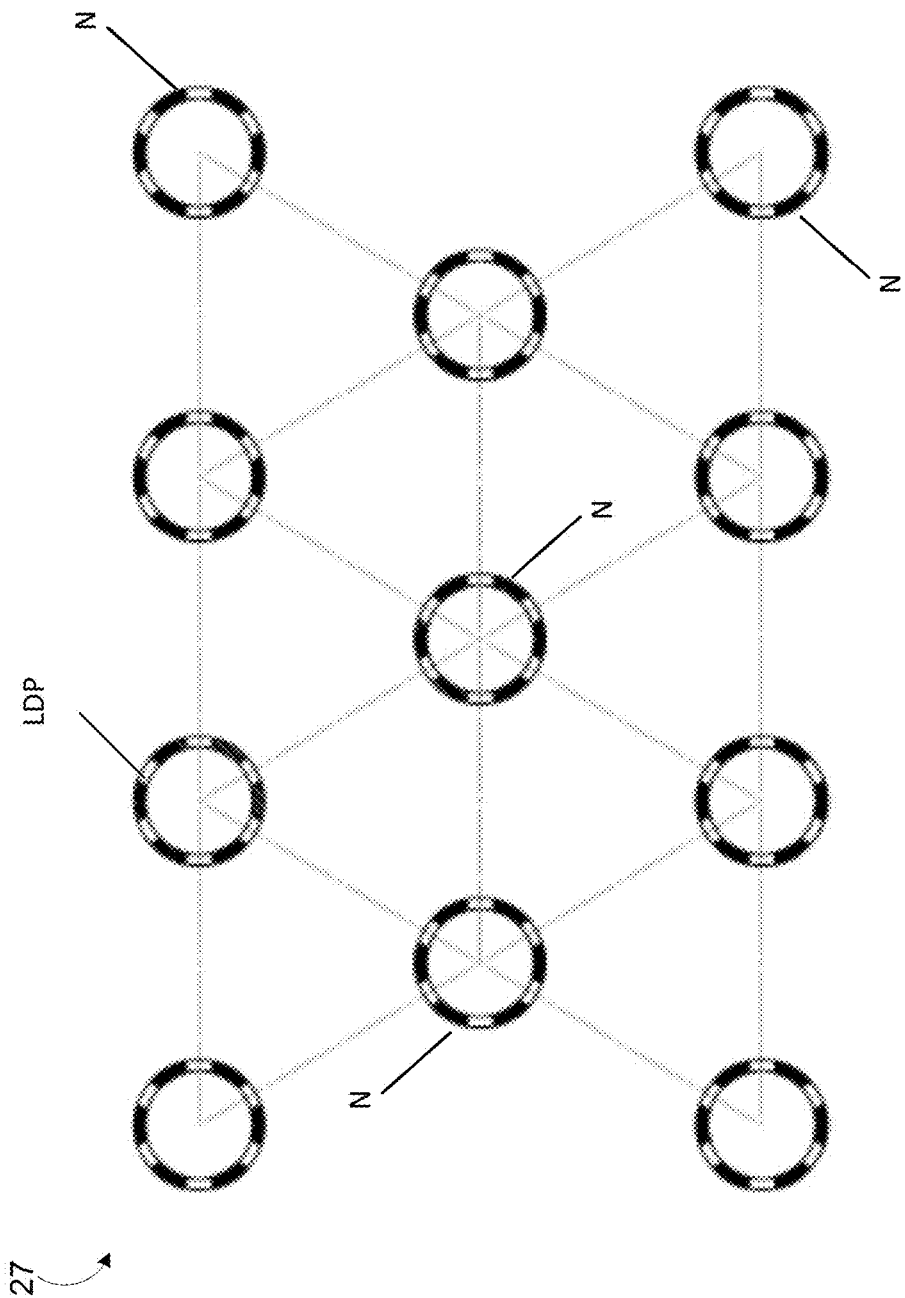
FIG. 10 is a cross section schematic diagram of exemplary RF electrode needles with liquid delivery ports mounted on an electrode applicator holder in a hexagonal pattern according to an illustrative embodiment of the disclosure.

An example needle with liquid delivery ports suitable for delivering various solutions is shown in FIG. 8. For example, in an embodiment, within a hexagonal array, a schematic diagram of exemplary RF electrode needles with liquid delivery ports mounted on an electrode holder in a hexagonal pattern is shown in FIG. 9. The periphery openings can be made at about 60° angle increments and oriented along the hexagonal electrode array grid. In this way, two adjacent needles (e.g., horizontally adjacent and/or diagonally adjacent) can have openings that are oriented toward one another such that the space therebetween can be saturated by liquid delivered from one or both of the adjacent needles in the array as is shown in FIG. 10. In an exemplary embodiment, openings around the periphery of each electrode may be preferentially oriented towards the nearest neighbor electrodes in the electrode array, as shown for example in FIG. 10.

FIG. 8 is a diagram of a RF electrode needle 20 with liquid delivery ports LDP or cutouts around its periphery, in accordance with an embodiment of the present disclosure. The liquid may include a conductive solution, medicament or other compounds for treating acne, improving healing, or otherwise cooling or changing one or more tissue properties pre, during, or post treatment. Various solutions may be delivered by one or more needles in the array. A reservoir of a given solution and a pump assembly may be in fluid communication with a given LDP port. In some embodiments, the needle's shafts may be insulated such that no energy is delivered in the epidermis and the superficial dermis, where there are no sebaceous glands. The non-isolated needle tip regions are inserted to deliver energy approximately at the range of depths of the sebaceous glands SG in the dermis. In most embodiments, the depth of the sebaceous glands in the dermis varies between about 0.5 and about 1.5 mm (down to about 2 mm) or between about 0.75 to about 1.25 mm depth. In various embodiments, an array of electrodes or microneedles are referred to as a needle array.

FIG. 9 is a schematic diagram of exemplary RF electrode needle array 21. The needles N that are shown include liquid delivery ports LDPs. The needles N are mounted on an electrode applicator holder or substrate 23 in a hexagonal pattern. As shown, in FIG. 9, the liquid delivery ports LDPs of the mounted electrodes are oriented to point to the nearest electrode.

FIG. 10 is a cross section schematic diagram of exemplary RF electrode needle array 27 with liquid delivery ports LDP mounted on an electrode applicator holder in a hexagonal pattern. Each needle is shown with six LDPs around its circumference. The number of LDPS per needle N may vary between 1 and about 16 LDPs in various embodiments. Various line segments connect the centers of the needle cross-sections to define an arrangement of hexagons and triangles. The cross-sectional plane includes various triangles that span the centers of the needles such that six triangles define a hexagonal arrangement of needles N. The cross-sections (and the sides of the triangles) are positioned in the middle of the liquid delivery ports and is perpendicular to the electrodes' axes. The walled portions of the RF electrodes (those portions that are not liquid delivery ports) appear on the schematic as darker hatched areas, the liquid delivery ports appear as lighter outline areas. The liquid delivery ports of the mounted electrodes are oriented to point to the nearest electrode. Dashed-dotted lines are drawn connecting the centers of the RF electrodes with liquid delivery ports in order to emphasize the orientation of the certain of the liquid delivery ports with respect to the nearest electrodes.

Figure 11:
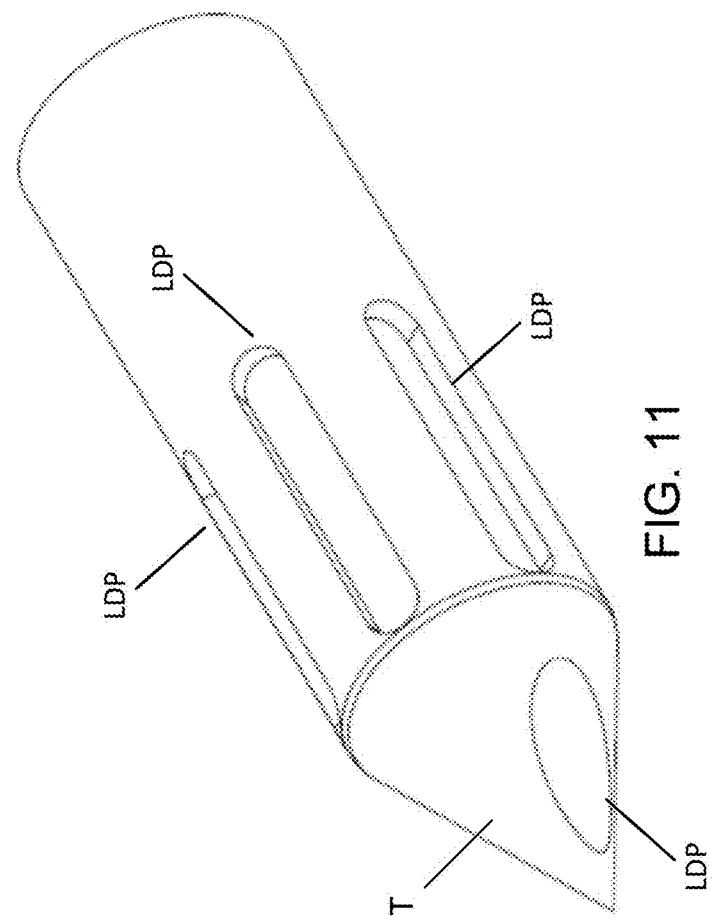
FIG. 11 is a schematic diagram of an exemplary RF electrode needle with liquid delivery ports around its periphery and a liquid delivery port at its tip according to an illustrative embodiment of the disclosure.

FIG. 11 is schematic diagram of an exemplary RF electrode needle 30 with liquid delivery ports LDPs around its periphery and a liquid delivery port LDP at its tip T. The port at the tip is shown in an off-center orientation at the tip T.

Figure 12:
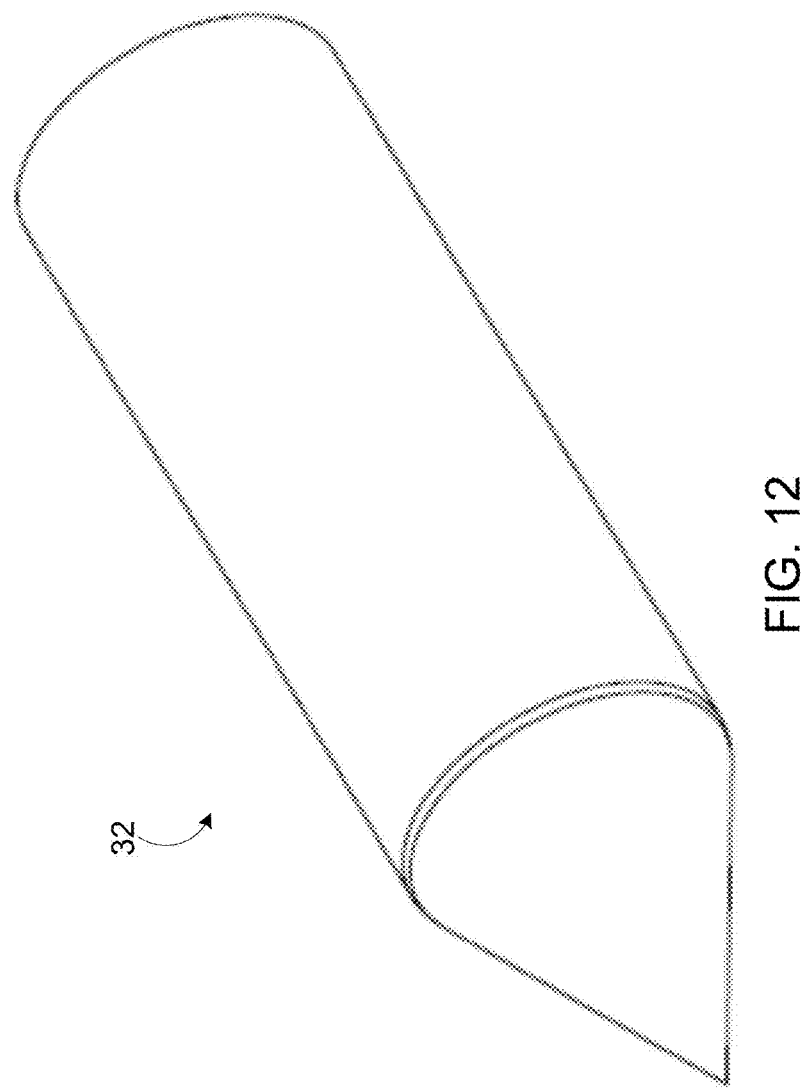
FIG. 12 is a schematic diagram of an exemplary RF electrode needle without liquid delivery ports according to an illustrative embodiment of the disclosure.

FIG. 12 is schematic diagram of an exemplary RF electrode needle 32 without liquid delivery ports. The length of the exemplary needle, and likewise the other needles described herein, may range from about 1 mm to about 50 mm, the length of the exemplary needle that is inserted into the subjects skin tissue may range from about 1 mm to about 5 mm. The thickness or the diameter of the exemplary needle, and likewise the other needles described herein, may range from about 0.1 to about 1 mm.

Figure 13:
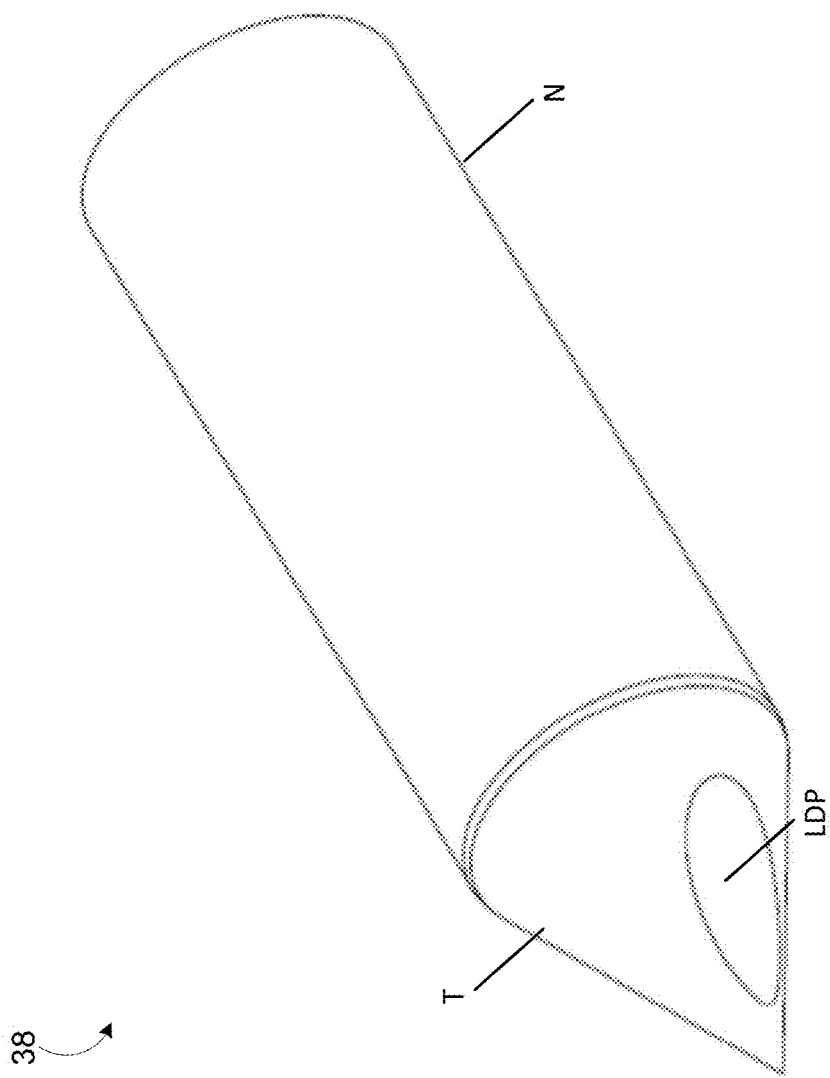
FIG. 13 is a schematic diagram of an exemplary RF electrode needle with a liquid delivery port at its tip according to an illustrative embodiment of the disclosure.

FIG. 13 is schematic diagram of an exemplary RF electrode needle 38 with a liquid delivery port LDP at its tip T. As shown, the LDP is oriented off center in the embodiment shown.

Figure 14:
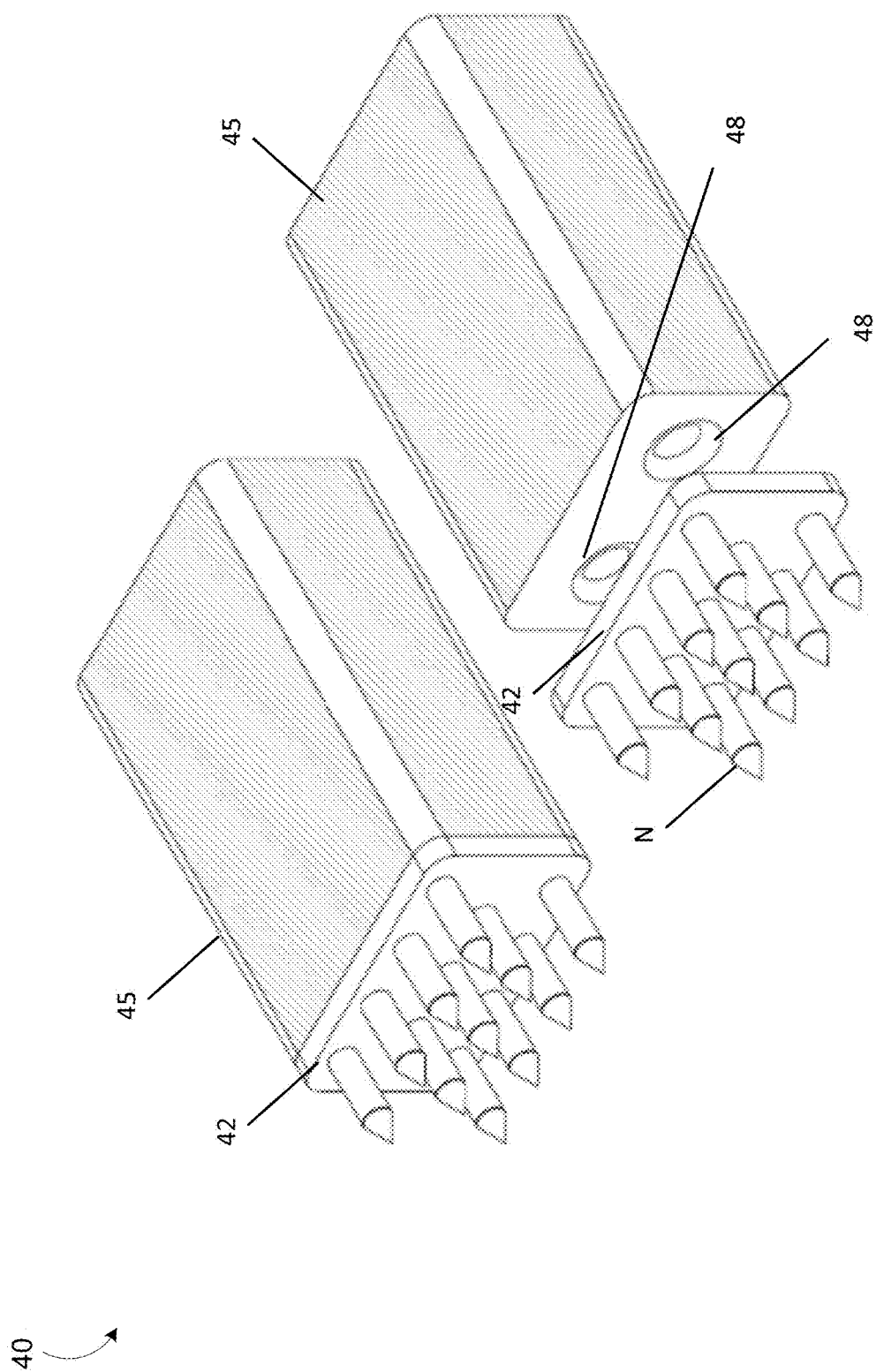
FIG. 14 is a schematic diagram of exemplary RF electrode needles mounted on an electrode holder with the capability to disconnect the electrode applicator holder with the attached electrodes from the handpiece according to an illustrative embodiment of the disclosure.

FIG. 14 is a schematic diagram of exemplary RF electrode needle array 40 mounted on an electrode holder or assembly 42. The electrode holder or assembly 42 is releasably coupled to a support structure. In some embodiments, the holder 42 has the capability to disconnect the electrode applicator holder with the attached electrodes from the handpiece or another support or structure 45. The RF electrodes may be inserted into the patient's skin. Mechanical couplers 48 such as a spring-loaded coupler or a fiction fit receptacle may work in conjunction with the electrode holder 42 to couple it to the handpiece 45.

In some embodiments, the electrode applicator assembly 42 is replaced or sterilized between patients. The treatment handpiece contains complex mechanical and electronic components, and optional liquid delivery components. The handpiece 45 facilitates electrode insertion in the skin, RF diagnostic, optional liquid delivery, therapeutic energy delivery and electrode retraction from the skin. The mechanical and electronic components that facilitate insertion of the electrodes (e.g., the microneedles) into the skin and retraction from the skin are not specifically shown here, but are known to those of skill in the art and are present in micro needling devices such as the Potenza™ RF microneedling system manufactured by Jeisys Medical, Inc. It would be economically advantageous for the portion of the handpiece that does not come into contact with the patient to be reusable such that it does not have to be replaced between patients. Accordingly, as shown, the portion of the treatment applicator that includes the microneedle array is releasably coupled to the handpiece.

In various embodiments, the conductive liquid delivered through the hollow electrodes may contain anesthetic to alleviate treatment pain that may be associated with the procedure. In various embodiments, the individual electrode needle for cold liquid delivery can either be open at the tip as shown in for example in FIG. 13, open around its periphery as shown for example in FIG. 8, or a combination of both as shown for example in FIG. 11. Alternatively, an electrode without liquid delivery is shown for example, in FIG. 12.

In various embodiments, spurious electrode polarization potentially can be a source of errors in characterization of the impedance and the dielectric properties of the tissue evaluated between the electrodes. The choice of electrode material and finish can improve spurious electrode polarization. For example, platinum electrodes coated with a rough layer of platinum black may decrease the effect of spurious electrode polarization.

Figure 15:
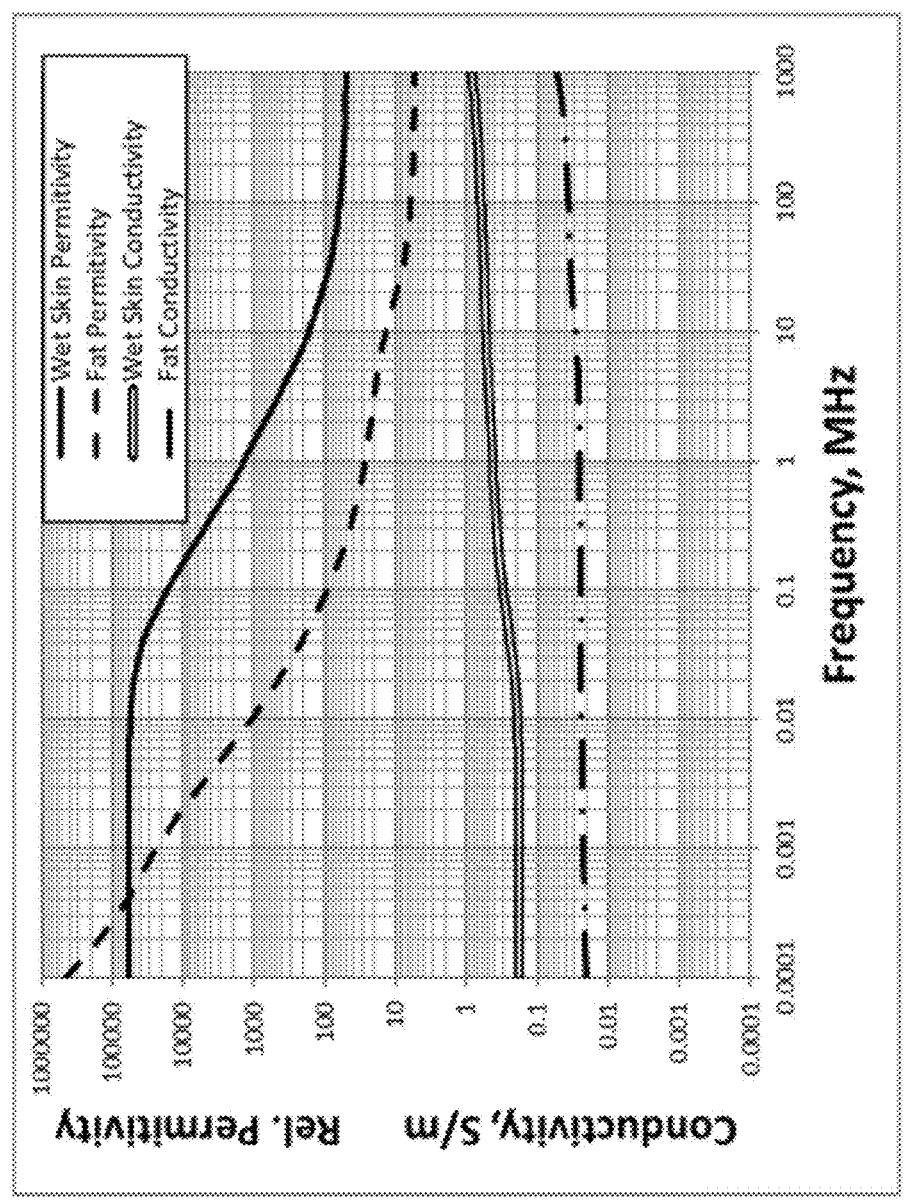
FIG. 15 is plot showing dielectric properties including permittivity and conductivity of wet skin (as a surrogate for dermal tissue) and fat (as a surrogate for sebaceous tissue) over a frequency range from about 0.0001 MHz to about 1000 MHz (e.g., 100 Hz to 1 GHz) with all data sourced from Gabriel S, Lau R W, Gabriel C. "*The dielectric properties of biological tissues: III. Parametric models for the dielectric spectrum of tissues*". Physics in Medicine & Biology. 1996 November; 41(11):2271 and Gabriel C, Peyman A, Grant E H. *Electrical conductivity of tissue at frequencies below 1 MHz Physics in medicine & biology.* 2009 Jul. 27; 54(16):4863.

FIG. 15 is a chart showing the dielectric properties including permittivity and conductivity of fat and wet skin. The wet skin data at frequencies lower than about 1 MHz is taken as data for the lower skin layers without the stratum corneum. Specifically, the wet skin data at frequencies lower than about 1 MHz (from about 0.0001 MHz to about 1 MHz) is taken as data for the lower skin layers where prior to the data collection the stratum corneum has been removed. The wet skin data for frequencies greater than about 1 MHz (from about 1 MHz to about 1000 MHz) is taken from skin layers that include intact stratum corneum, but this data shows no discontinuity from the data taken at less than about 1 MHz, because at higher frequencies such as greater than about 1 MHz the data with and without stratum corneum is the same. FIGS. 3, 16, 17, and 18 are calculated based on the data in FIG. 15. Accordingly, the data depicted in FIGS. 3, 16, 17, and 18 are likewise in the absence of the stratum corneum.

Fat is used as a surrogate for sebaceous tissue and wet skin is used as a surrogate for dermal tissue. The relative permittivity and conductivity of fat and wet skin for frequencies between about 100 Hz and about 1 GHz are shown plotted in FIG. 15. The permittivity and conductivity of fat and wet skin enable us to look at a large frequency range. This enables us to make a smart choice of the likely frequency ranges where there is a strong contrast between sebaceous tissue and dermal tissue.

Figure 16:
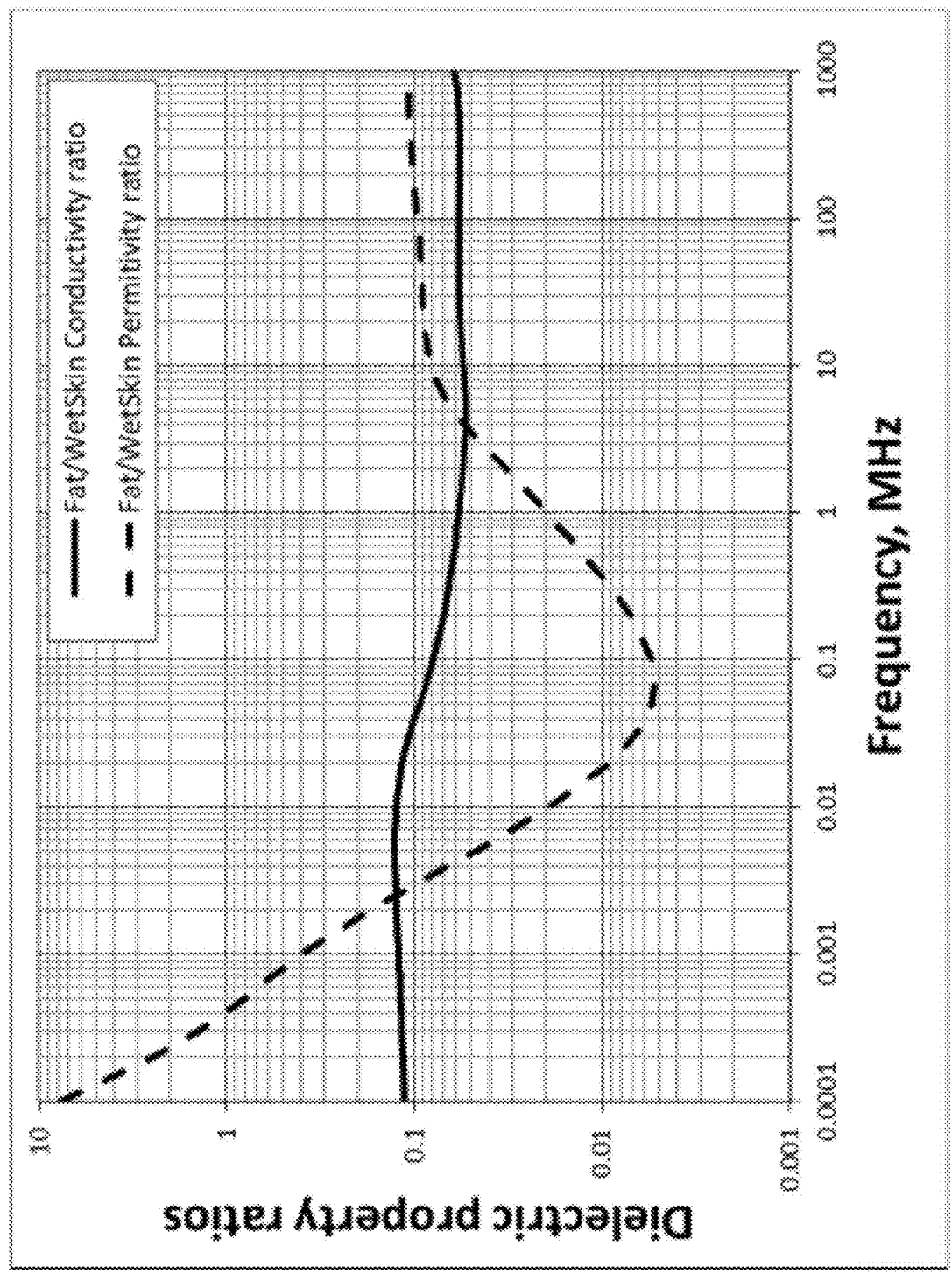
FIG. 16 is a plot showing ratios of the dielectric properties of fat (as a surrogate for sebaceous glands) vs wet skin (as a surrogate for dermal tissue), specifically, the ratio of fat conductivity to wet skin conductivity (in solid line) and the ratio of fat permittivity to wet skin permittivity (in broken line) over a frequency range from about 0.0001 MHz to about 1000 MHz (e.g., 100 Hz to 1 GHz).

FIG. 16 is a plot showing on the y-axis the ratios of the dielectric properties of fat (fat as a surrogate for sebaceous glands) vs. wet skin (wet skin as a surrogate for dermal tissue), specifically, the ratio of fat conductivity to wet skin conductivity (in solid line) versus frequency in MHz on the x-axis and the ratio of fat permittivity to wet skin permittivity (in broken line) versus frequency in MHz on the x-axis. As shown in FIG. 16, there are extensive frequency ranges, shown on the x-axis as frequency in MHz, where the one or both of two dielectric properties of fat and wet skin, namely, the fat/wet skin conductivity ratio and/or the fat/wet skin permittivity ratio differ by a factor of more than 2 or 5 or 10 at a specific frequency and where the dielectric property ratio is different than 1 (e.g., is greater than or less than a dielectric property ratio of 1).

Alternatively, targeting of a sebaceous gland is preferred at a frequency where the dielectric properties of sebum and skin dermis are different and where the dielectric property ratio is different than the range from about 0.9 to about 1.1, about 0.8 to about 1.2, or about 0.6 to about 1.4. And targeting of a sebaceous gland in preferred conditions for frequencies where the dielectric properties of fat and wet skin vary by more than a factor of 10, for differences larger than a factor of 5 and for differences larger than a factor of 2, for example. It is noteworthy, referring still to FIG. 15, that for the purpose of diagnostic use the dielectric property ratio data shown on the y-axis is particularly useful from a ratio of 10 or greater and from a ratio of 0.1 or less, in this region the properties of fat/wet skin conductivity ratio and fat/wet skin permittivity ratio vary by a relatively large degree, for example, in many regions greater than a factor of 10. It is preferable to target a sebaceous gland (fat is a surrogate for sebaceous tissue) as viable for treatment at a frequency where the dielectric properties of sebum and skin dermis are different and where the conductivity ratio of fat/wet skin and/or the permittivity ratio of fat/wet skin is more than 2, more than 5, or more than 10, for example. All of the forgoing factors may vary be about 5% or 10% in a given embodiment.

Figure 17:
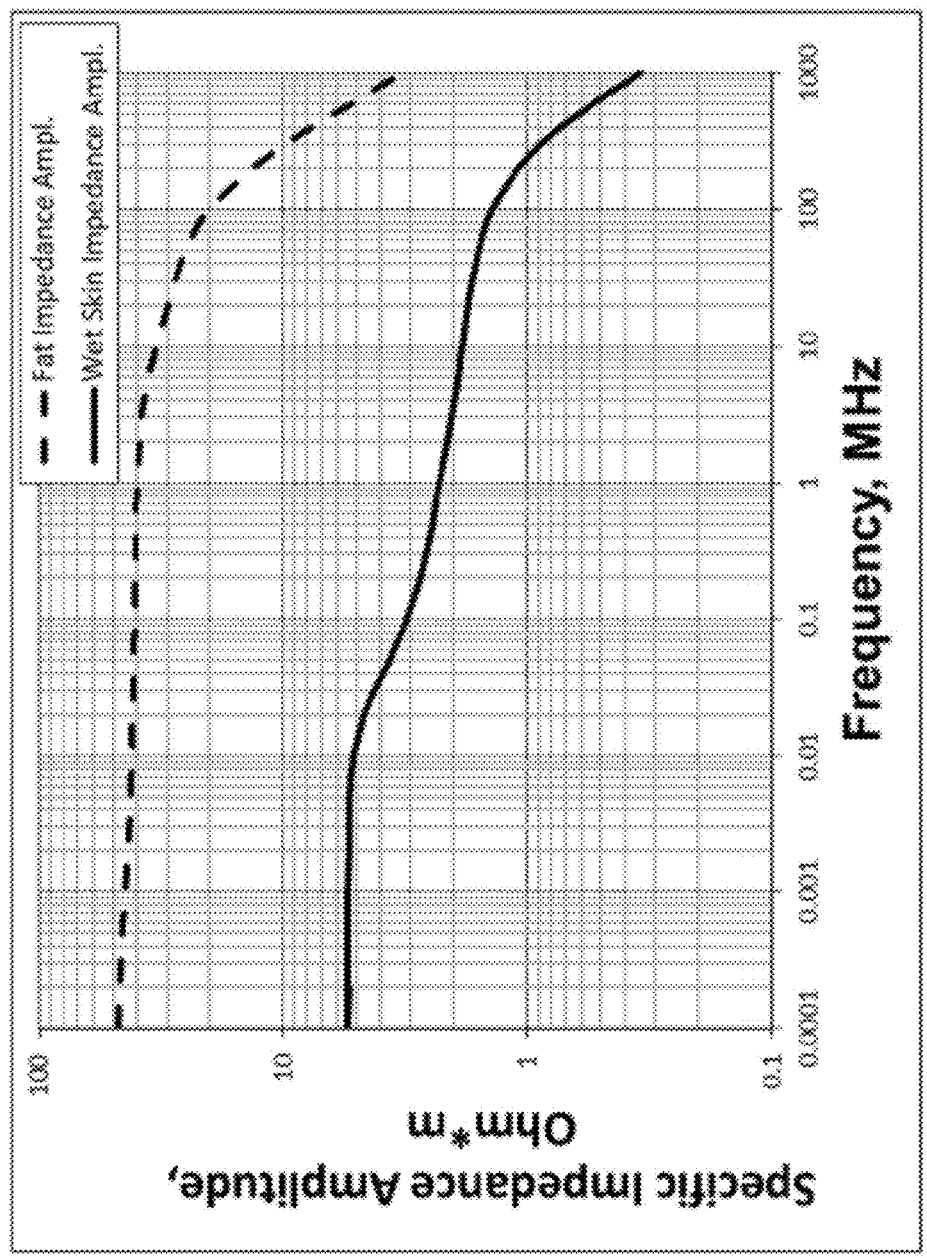
FIG. 17 is a plot of specific electrical impedance amplitude of wet skin (as a surrogate for dermal tissue) in solid line and fat (as a surrogate for sebaceous tissue) in broken line over a frequency range from about 0.0001 MHz to about 1000 MHz (e.g., about 100 Hz to about 1 GHz) according to an illustrative embodiment of the disclosure.

As shown in FIG. 17, in the considered frequency range between about 100 Hz to about 1000 MHz fat impedance is larger than wet skin impedance. In that case the sebaceous glands will be heated by heat diffusion from the surrounding dermis. In some scenarios, heat diffusion from surrounding tissues provides more efficient tissue heating. Limiting the thermal damage in the dermis only to regions containing ESGs between RF electrodes in a fractionated arrangement allows the thermally damaged dermal regions to heal quickly after the treatment.

In various embodiments, when using electromagnetic energy for targeting sebaceous glands, the controller system uses measured tissue impedance. Targeting of a sebaceous gland is based on the difference of impedance between sebum when compared to dermal tissue. For example, the relative permittivity $\varepsilon_r$ and conductivity $\sigma$ of tissue, can be used to calculate the tissue admittivity $\gamma$.

$$\gamma = \sigma + i\omega \varepsilon_r \varepsilon_0$$

where $\varepsilon_0$ is the electrical permittivity of vacuum and $\omega = 2\pi f$ is the angular frequency, and i is the imaginary unit $i=\sqrt{-1}$. The specific electrical impedance z is the inverse of the admittivity $\gamma$.

$$z = \frac{1}{\gamma} = \frac{1}{\sigma + i\omega \varepsilon_r \varepsilon_0} = \frac{\sigma + i\omega \varepsilon_r \varepsilon_0}{\sigma^2 + (\omega \varepsilon_r \varepsilon_0)^2} = |z|\exp(i\theta)$$

During a diagnostic procedure, the measured properties of tissue may be the amplitude of the specific electrical impedance $|z|$ and the tangent of its phase angle $\theta$. These terms can be written in terms of the tissue relative permittivity and conductivity as follows:

$$|z| = \sqrt{zz^*} = \frac{1}{\sqrt{\sigma^2 + (\omega \varepsilon_r \varepsilon_0)^2}}$$

$$\tan\theta = \frac{\mathrm{Im}(z)}{\mathrm{Re}(z)} = -\frac{\omega \varepsilon_r \varepsilon_0}{\sigma}$$

Figure 18:
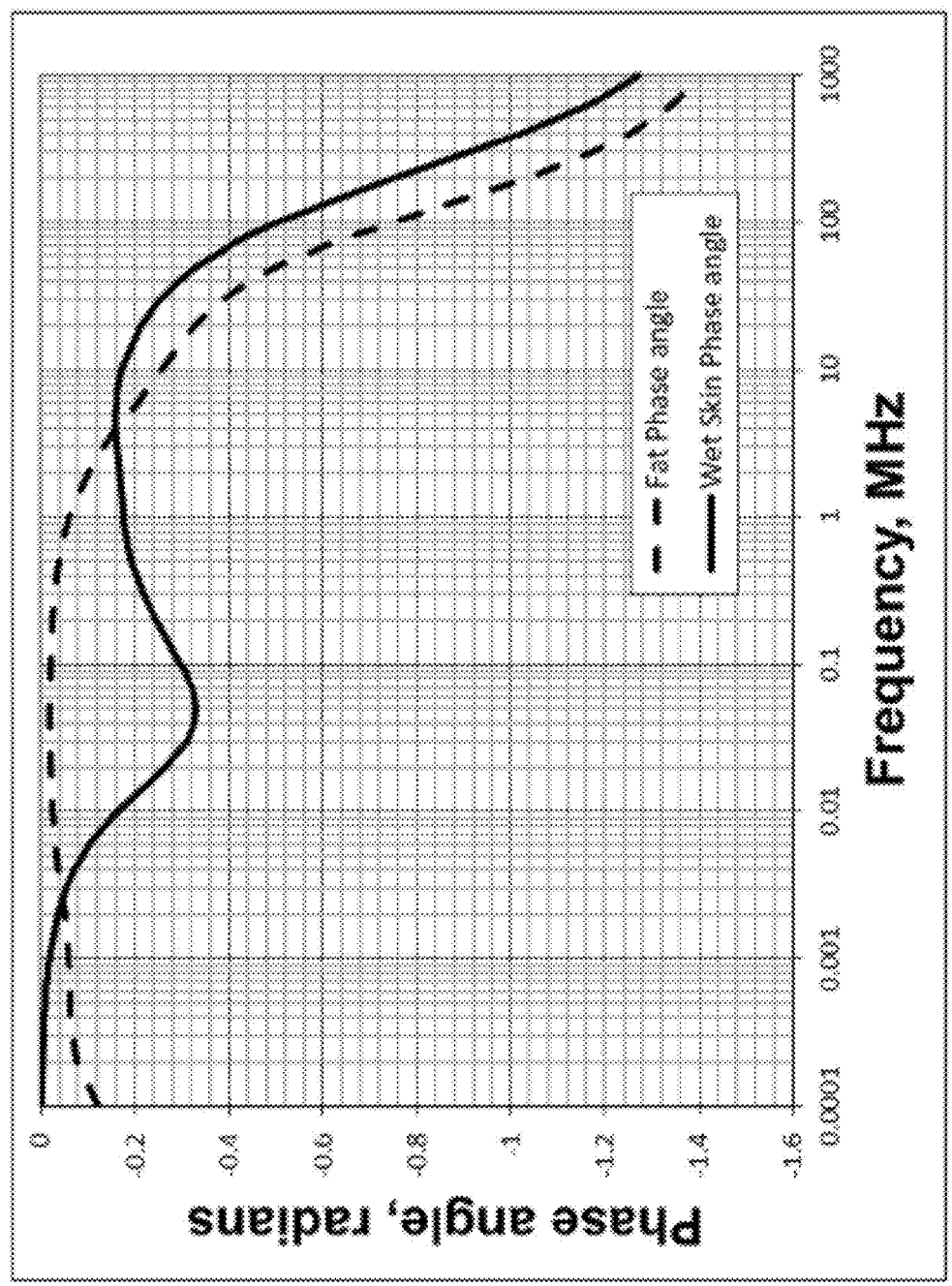
FIG. 18 is a plot showing specific impedance phase angle of wet skin (as a surrogate for dermal tissue) in solid line and fat (as a surrogate for sebaceous tissue) in broken line over a frequency range from about 0.0001 MHz to about 1000 MHz (e.g., about 100 Hz to about 1 GHz) according to an illustrative embodiment of the disclosure.

The calculated specific electrical impedance amplitude $|z|$ and phase angle $\theta$ for wet skin and fat are plotted on FIGS. 17 and 18. The ratios of the specific electrical impedance amplitude and phase angle of fat versus wet skin are plotted on FIG. 15.

FIG. 15 is a chart of frequency versus impedance ratios of fat versus wet skin. As shown, FIG. 15 shows that there are frequency ranges where the specific impedance of fat and wet skin differs by a factor of more than 2 or 5 or 10. The targeting of sebaceous glands is optimized when specific impedance varies by more than a factor of 10, less ideally for differences larger than a factor of 5, and least preferred for differences larger than a factor of 2. Based on FIG. 15, in the considered frequency range between about 100 Hz and about 1000 MHz fat impedance amplitude is larger than wet skin impedance amplitude. In that case the sebaceous glands can be heated by heat diffusion from the surrounding dermis that will be heated more efficiently. Limiting the thermal damage in the dermis only to regions containing ESGs between RF electrodes in a fractionated arrangement allows the thermally damaged dermal regions to heal quickly after the treatment.

In FIGS. 3, 15, 16, 17, and 18 the plots demonstrate the relationship of dermis and sebaceous glands as expressed by their relative electrical properties, however the data is actually wet skin data acting as a surrogate for dermis and fatty tissue data acting as a surrogate for sebaceous glands. In the future, data from dermal tissue and sebaceous gland tissue or other more accurate data for the dielectric properties of sebum and dermis may itself become available and as a result the plots may alter somewhat, but the technical analysis to addressing and treating the ESGs with RF energy will remain consistent.

Extensions of the described device and method may be envisioned for other localized tissue structures and for various tissue, organs, cells, organelles, cellular outputs and products and other conditions. For example, localization guided selective electrothermolysis treatment of sweat glands may be applied to regions of the skin with excessive sweating. Another example is regions of tissue having unwanted blond and white hairs. These tissue regions often have insufficient pigment contrast for laser based selective photothermolysis and thus may be treated as disclosed herein using localization guided selective electrothermolysis.

Unwanted Hair

A similar approach as described above for treatment of enlarged sebaceous glands can be applied also for treatment of unwanted hair. In a first diagnostic step the locations of hair follicles are determined by using the lower conductivity of the hair shafts compared to the surrounding dermis. In the second treatment step the higher energy treatment pulses are delivered only to the electrodes identified to be in close proximity to hair follicles previously identified by the lower conductivity of their respective hair shafts compared to the surrounding dermis. The treatment pulses are used to deliver higher RF power that will heat selectively, and coagulate, all or a portion of the blood vessels in the proximity of hair follicles. Such treatment technique will be particularly useful for treatment of white, red, blonde and lightly colored hair that is difficult to treat with conventional laser hair removal. In general, unwanted body hair can be a source of embarrassment and social anxiety for people. The ability to cosmetically treat hair follicles to remove or prevent unwanted hair helps promote self esteem and reduces embarrassment and social anxiety. As such, the cosmetic treatment of unwanted hair and other cosmetic treatments disclosed herein offer numerous benefits to people and help overcome ridicule and criticism from others in social situations.

Vascular Lesions

A similar approach as described above for treatment of enlarged sebaceous glands can be applied also for treatment of unwanted vascular lesions. Unwanted vascular lesions on the skin are commonly associated with increased blood vessel diameter or increased blood vessel density in the affected region. Examples of vascular lesions are telangiectasias, diffuse erythemas, hemangiomas, portwine stains etc. In both cases, either because of increased blood vessel diameter or increased blood vessel density, the volume fraction of blood in the dermis is increased in the affected region.

Figure 5:
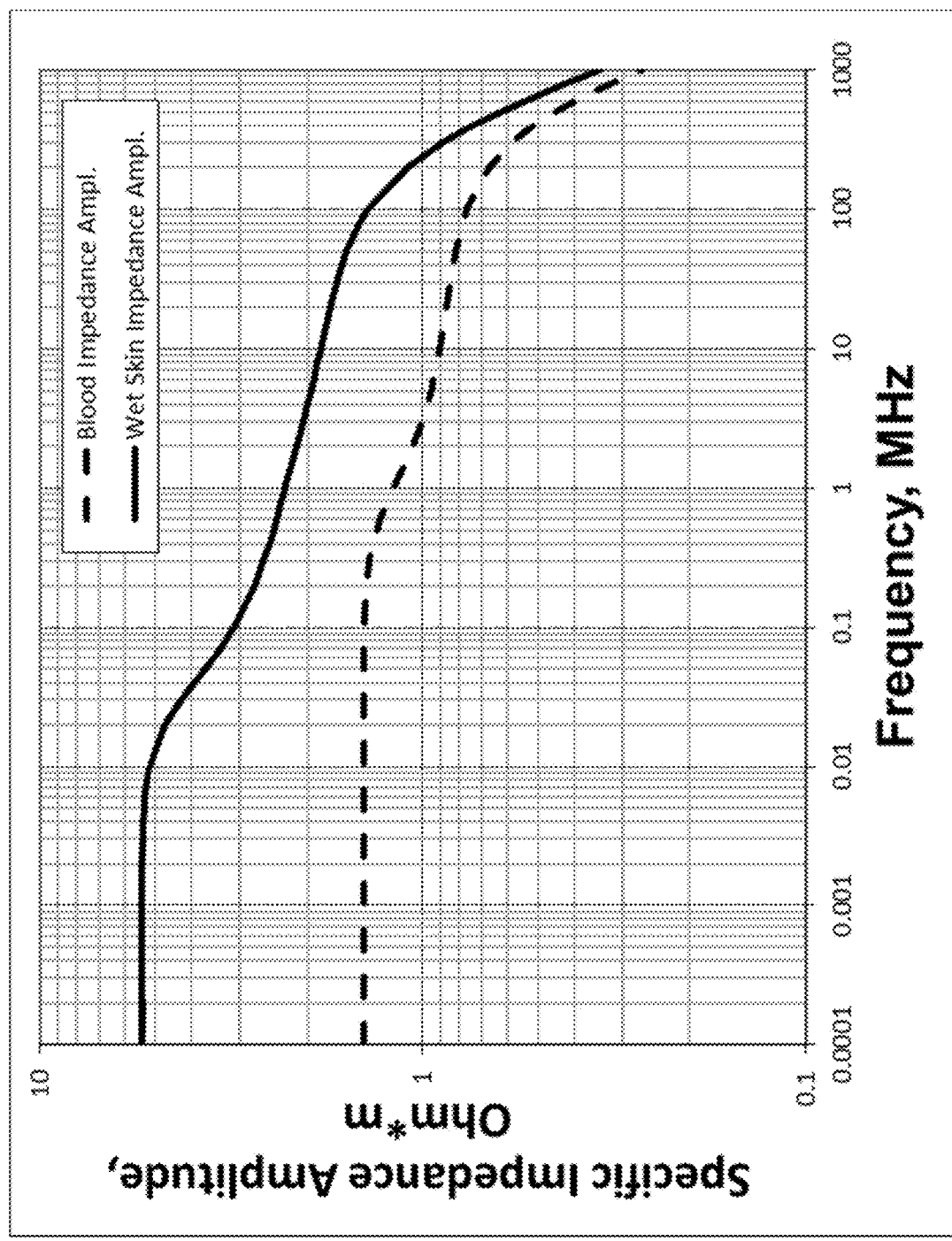
FIG. 5 is a plot showing specific impedance amplitude of blood vs wet skin (as a surrogate for dermal tissue) as two different curves over a frequency range from about 0.0001 MHz to about 1000 MHz (e.g., 100 Hz to 1 GHz) according to an illustrative embodiment of the disclosure.
Figure 6:
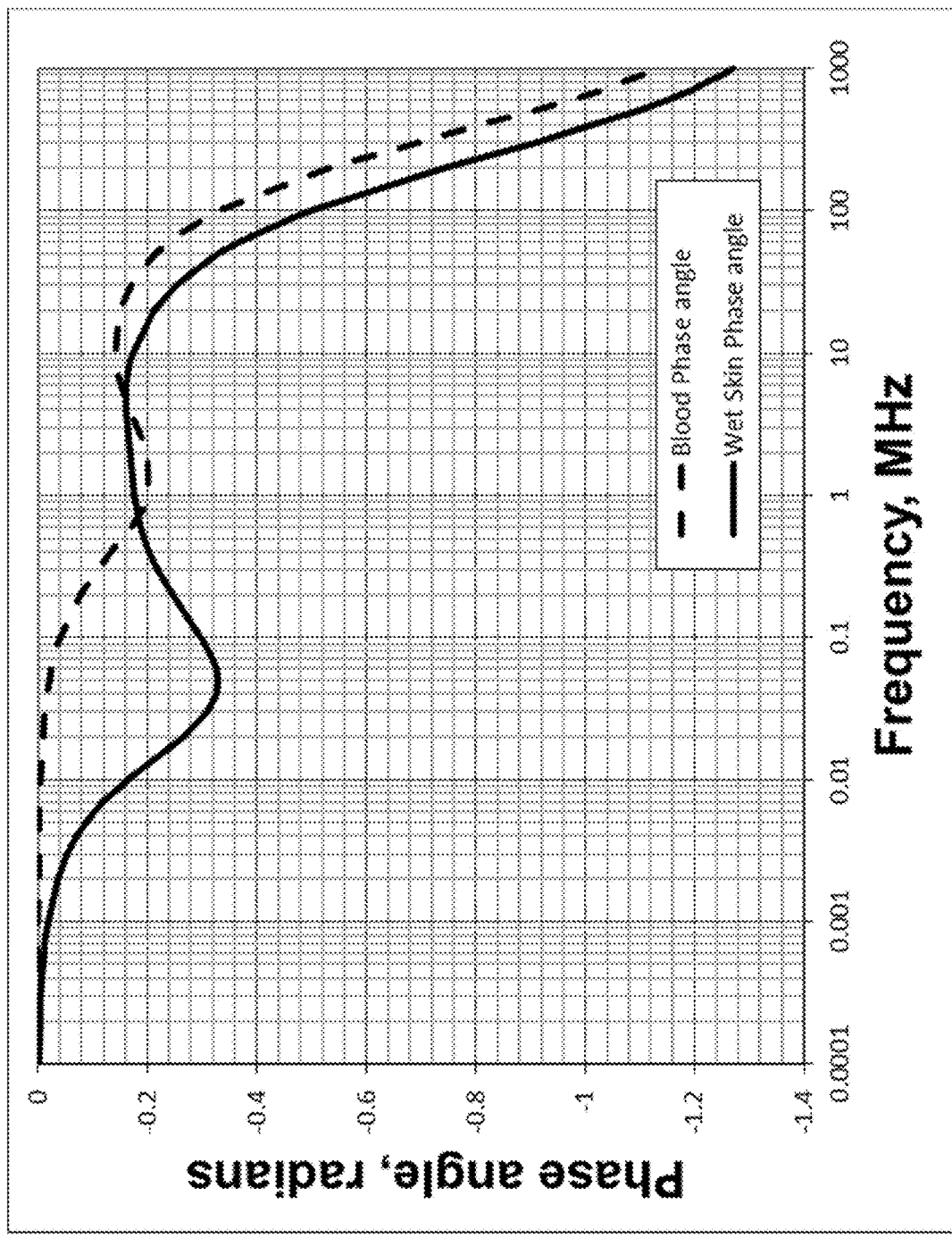
FIG. 6 is a plot showing phase angle of blood vs wet skin (as a surrogate for dermal tissue) as two different curves over a frequency range from about 0.0001 MHz to about 1000 MHz (e.g., 100 Hz to 1 GHz) according to an illustrative embodiment of the disclosure.
Figure 7:
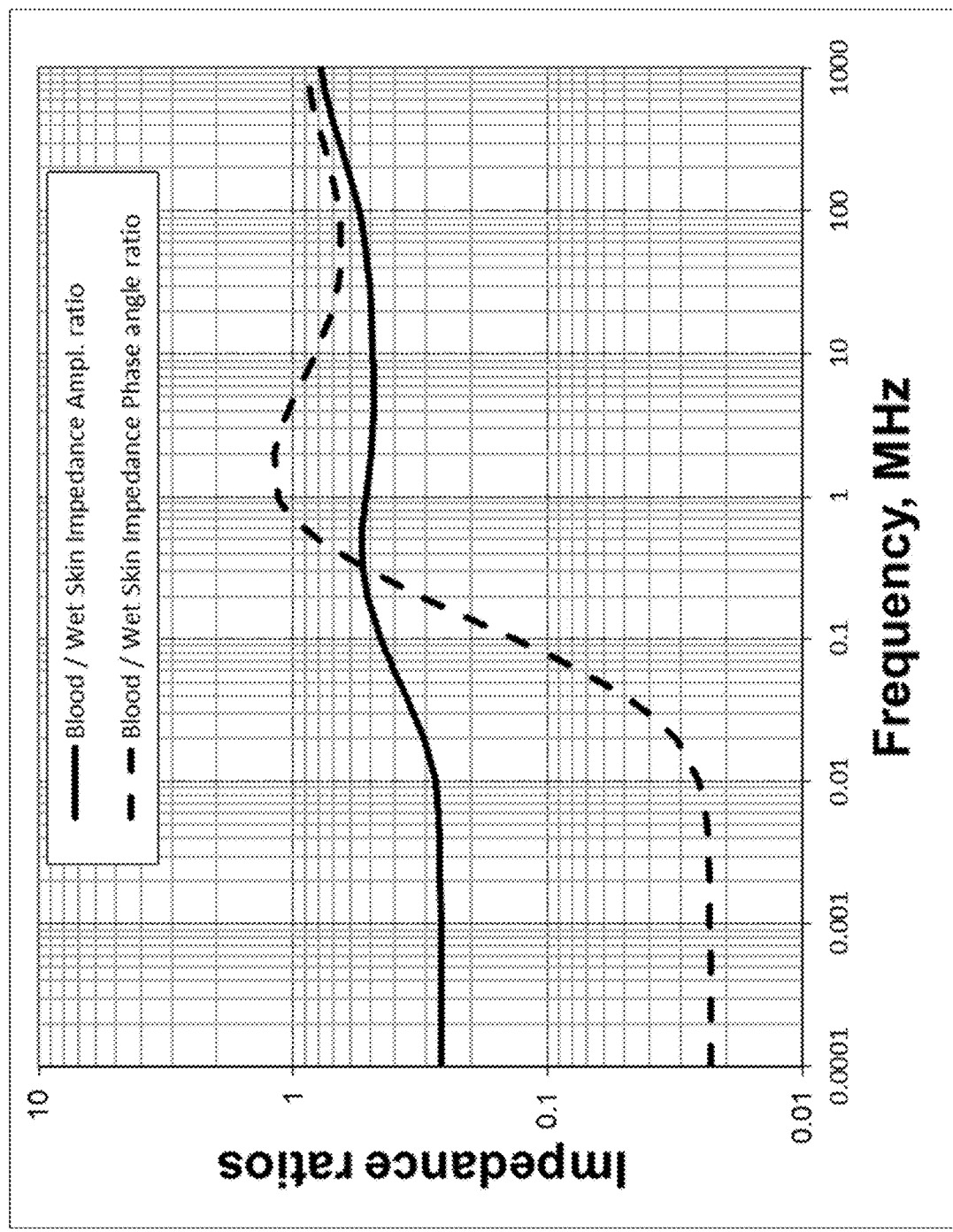
FIG. 7 is a plot showing impedance amplitude ratio and impedance phase angle ratio of blood vs wet skin (as a surrogate for dermal tissue) as two different curves over a frequency range from about 0.0001 MHz to about 1000 MHz (e.g., 100 Hz to 1 GHz) according to an illustrative embodiment of the disclosure.

In a first diagnostic step the locations of increased blood volume fraction can be located by using the difference of the dielectric properties of blood vs dermis and the corresponding impedance amplitude and phase, FIGS. 4, 5, and 6. The ratios of the specific electrical impedance amplitude and phase angle of blood vs dermis are plotted on FIG. 7. FIG. 7 indicates that there are extensive frequency ranges where the specific impedance of blood and dermis differs by a factor of more than 2. For example, for frequencies between about 100 Hz and about 50 MHz, the blood specific impedance is between about 25% and about 50% of the dermis impedance. Larger blood volume fraction will lead to larger impedance variation when surrounded by groups of 2 or more electrodes vs the array averaged impedance measured between similar groups of electrodes in the absence of elevated blood volume fraction. The regions with the highest blood volume fraction will be targeted for energy delivery.

In general, unwanted blood vessels, such as spider veins, or vascular lesions can be a source of embarrassment and social anxiety for people. The ability to cosmetically treat blood vessels and lesions to remove or prevent unwanted red spots, skin discoloration, spider veins, or other unwanted visible marks or blemishes promotes self esteem and reduces embarrassment and social anxiety. As such, the cosmetic treatment of blood vessels and lesions and other cosmetic treatments disclosed herein offer numerous benefits to people and help overcome ridicule and criticism from others in social situations.

The lower RF impedance of the blood in the blood vessels will lead to higher RF power delivered through the blood vessels located between the two, or more, electrodes that are identified near a targeted region with elevated blood volume fraction. RF power flow through blood vessels and the associated blood vessel heating will lead to injury of the blood vessels walls. The RF pulse on-time is preferentially selected to cause selective heating to the enlarged vessel based on the theory of selective photo-thermolysis, R. Rox Anderson et al., "*Selective Photothermolysis: Precise Microsurgery by Selective Absorption of Pulsed Radiation, Science*", Vol. 220 pp. 524-528, applied to the selective blood vessel heating by RF power. Higher frequency RF power delivery would be preferable due to the "skin effect" of larger current density in the periphery of an RF conductor. Thermal, mechanical and other injury to the blood vessels walls will lead to coagulation of the blood in the injured vessel within 5 to 100 seconds after the delivery of the RF power, Falati et al., "*Real-time in vivo imaging of platelets, tissue factor and fibrin during arterial thrombus formation in the mouse*", *Nature Medicine*•Volume 8•Number 10•October 2002, pp. 1175-1180 and Furie et al., "*Thrombus Formation in Vivo*", *The Journal of Clinical Investigation*, Vol. 115:12, December 2005, pp. 3355-3362. Selective coagulation of all or a portion of the enlarged blood vessels is expected to lead to decrease of the elevated blood volume fraction in the targeted region after it heals. The decrease of the elevated blood volume fraction is expected to lead to improved visual appearance of the unwanted vascular lesion.

Sweat Glands

Hyperhidrosis is commonly defined as excessive sweating beyond what is physiologically required to regulate body temperature. The social impact of hyperhidrosis on patient's lives is comparable to many dermatologic disorders such as psoriasis, acne, and vitiligo. Patient's sometimes make limiting lifestyle choices to avoid the risk of excess sweating in social situations. Accordable, cosmetic treatment of sweat glands to prevent or improve excess sweating can help build self esteem and reduce embarrassment. Common examples of areas of excess sweating are the axillae, or armpits, palms and soles.

It is generally accepted that there are two types of sweat glands: eccrine and apocrine glands. A third type "apoeccrine" gland has been identified and discussed as well. The eccrine glands secrete a clear, nonodorous sweat, whose primary function is thermoregulation of body temperature. The sweat glands are distributed all over the body with a variable number of glands per unit area. The apocrine glands secrete a milky sweat; these glands are primarily found in the axillae and genital region. Both of these gland types reside near the dermal/hypodermal, DH, interface. In a study of human axillae, all or most of the sweat glands were found to be in the subcutaneous tissue below the DH interface, Beer et al., "*Immunohistochemical Differentiation and Localization Analysis of Sweat Glands in the Adult Human Axilla*", https://journals.lww.com/plasreconsurg/Abstract/2006/05000/Immunohistochemical Differentiation and.52.aspx.

Localized treatment with RF power of sweat glands leading to their thermal damage, or necrosis, is expected to lead to improvement of the hyperhidrosis disorder. Microwave treatment without localization of sweat glands has been shown to lead to improvement of the hyperhidrosis disorder, Hong et al., "*Clinical Evaluation of a Microwave Device for Treating Axillary Hyperhidrosis*", 2012 by the American Society for Dermatologic Surgery, Inc. Published by Wiley Periodicals, Inc. ISSN: 1076-0512, *Dermatol Surg* 2012; 38:728-735, DOI: 10.1111/j.1524-4725.2012.02375.x. Microwave treatment without localization of the sweat glands involves heating of a large portion of the skin from the surface to the DH junction. The non-selective volume heating requires skin cooling and localized injection anesthetics for pain management. Localized treatment with RF power of sweat glands will avoid the non-selective volume heating and improve safety and patient comfort while maintaining or exceeding the efficacy of the microwave treatment.

The hypodermis or subcutaneous tissue consists of adipose tissue. The dielectric properties of fat (for adipose tissue) will be used as summarized in Gabriel et al., "*The dielectric properties of biological tissues: I Literature survey, Phys. Med. Biol.* 41 (1996) 2231-2249, and Gabriel S, Lau R W, Gabriel C. "*The dielectric properties of biological tissues: III. Parametric models for the dielectric spectrum of tissues*". Physics in Medicine & Biology. 1996 November; 41(11):2271 and Gabriel C, Peyman A, Grant E H. *Electrical conductivity of tissue at frequencies below 1 MHz Physics in medicine & biology.* 2009 Jul. 27; 54(16):4863. The dielectric properties of artificial sweat (for human sweat) will be used as summarized in Eldamak et al., "*Study of the Dielectric Properties of Artificial Sweat Mixtures at Microwave Frequencies*", Biosensors 2020, 10, 62. The relative permittivity and conductivity of fat and artificial sweat for frequencies between about 100 Hz and about 1 GHz are plotted in FIG. 19. When more accurate data for the dielectric properties of hypodermis and sweat become available the exact values may be updated, however the general concept of localization and RF treatment of sweat glands based on their dielectric properties will remain valid.

A similar approach as described above for treatment of enlarged sebaceous glands can be applied also for treatment of excessive sweating. In a first diagnostic step the localization of the sweat glands is based on the difference of the dielectric properties of sweat vs fat. In addition, during the diagnostic step it will be possible to determine if the non-insulated, energy delivering, tips of the electrodes are positioned in the dermis or the hypodermis due to the large difference in specific of fat vs dermis, FIG. 3. If the non-insulated tips of the electrodes are determined to be in the dermis they can be repositioned to penetrate in the hypodermis. Then, when the non-insulated tips of the electrodes are in the hypodermis, the impedance variation diagnostic using the electrode array will allow to determine the location of the sweat glands and their approximate size.

In the second treatment step the higher energy treatment pulses are delivered only to the electrodes that are identified to be inside sweat glands or to be in close proximity to sweat glands. Only a relatively small fraction of the electrodes in the array will turn out to be in the proximity of sweat glands and when they are energized only a small volume fraction of the hypodermis in the vicinity of these sweat glands will be thermally damaged.

In general, unwanted excess sweating can be a source of embarrassment and social anxiety for people. The ability to cosmetically treat sweat glands to remove or prevent unwanted sweating helps promote self esteem and reduces embarrassment and social anxiety. As such, the cosmetic treatment of excess sweating and other cosmetic treatments disclosed herein offer numerous benefits to people and help overcome ridicule and criticism from others in social situations.

Figure 19:
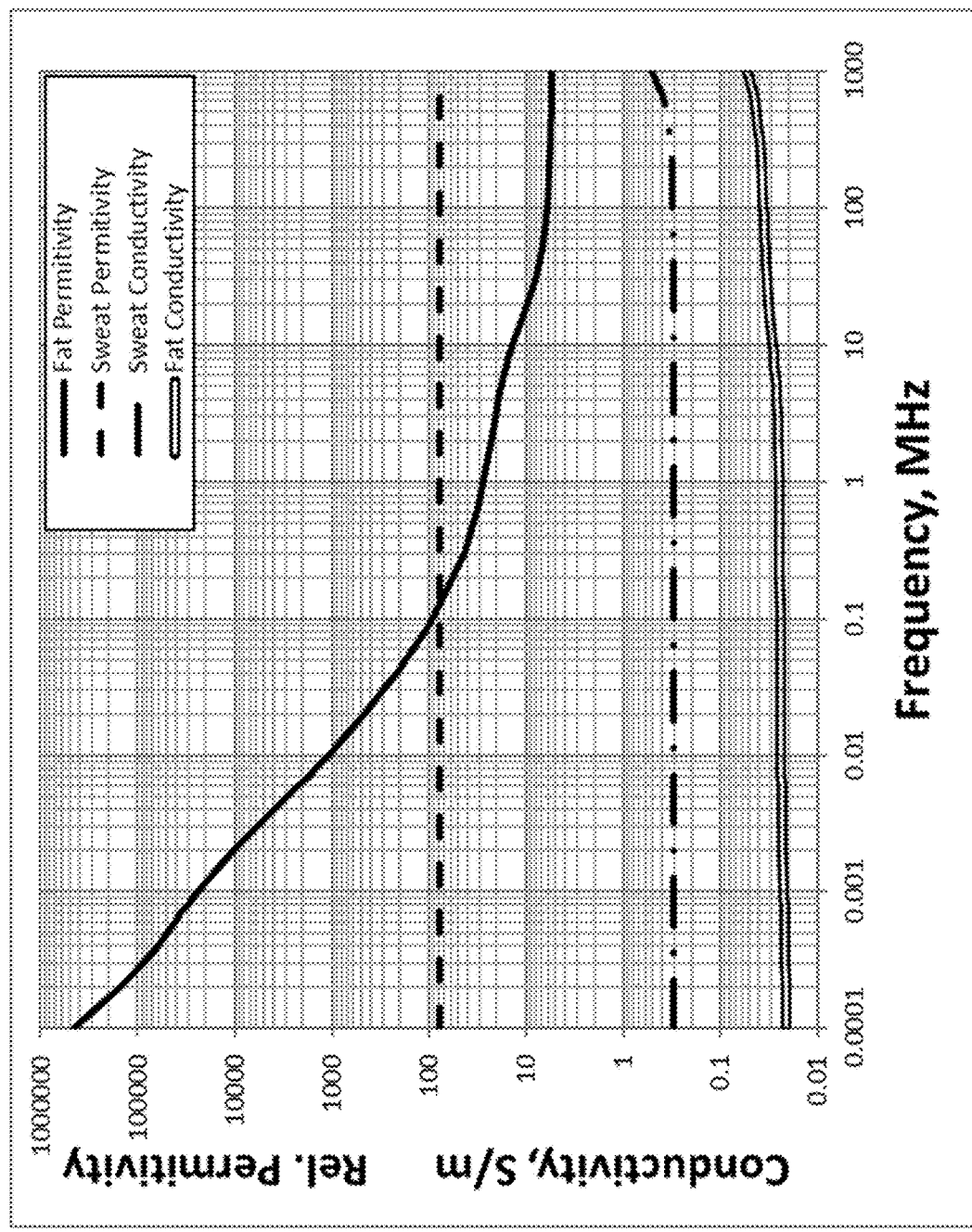
FIG. 19 is a plot showing relative permittivity and conductivity of fat and artificial sweat for frequencies between as four different curves over a frequency range from about 0.0001 MHz to about 1000 MHz (e.g., 100 Hz to 1 GHz) according to an illustrative embodiment of the disclosure
Figure 20:
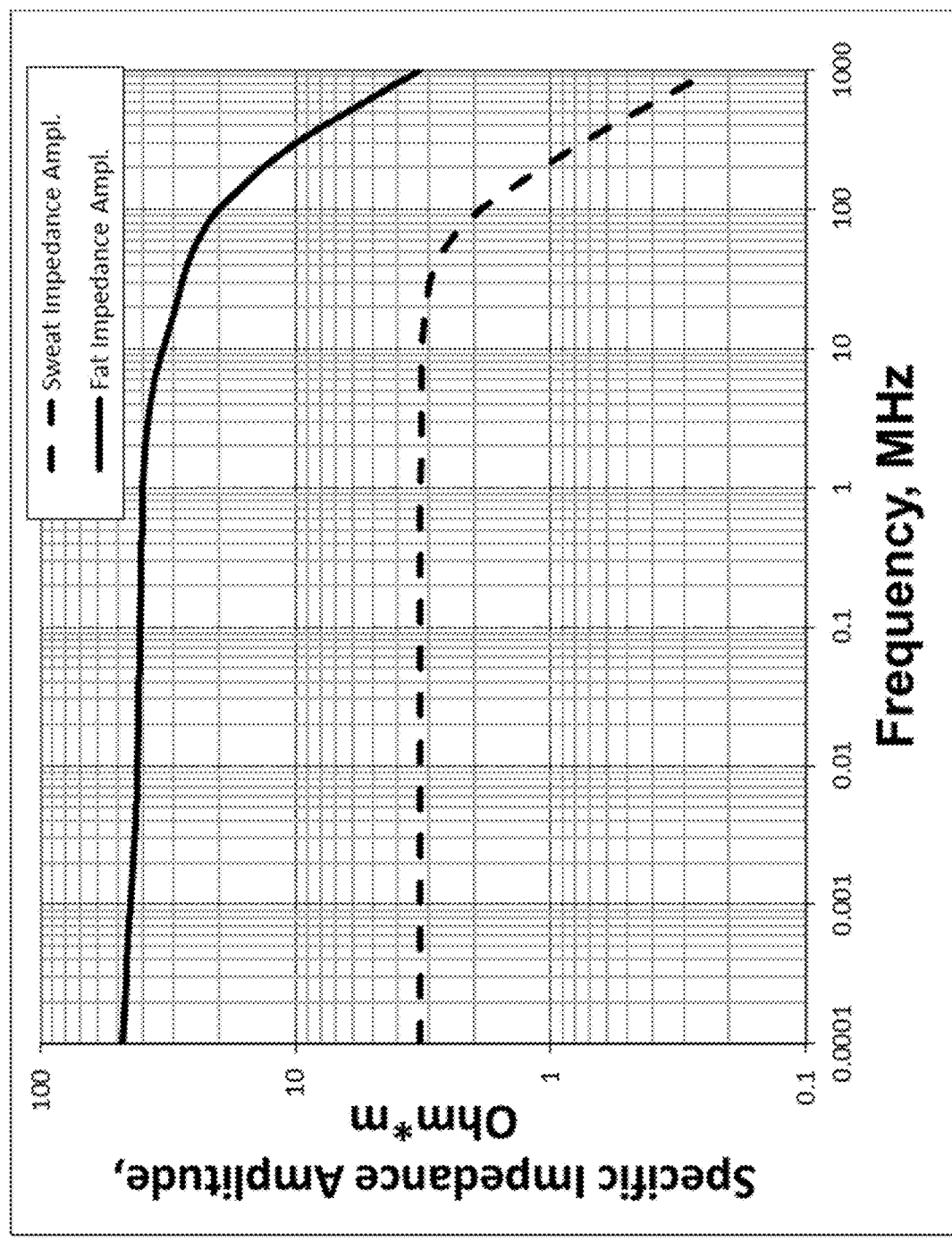
FIG. 20 is a plot showing specific impedance amplitude of sweat versus fat as two different curves over a frequency range from about 0.0001 MHz to about 1000 MHz (e.g., 100 Hz to 1 GHz) according to an illustrative embodiment of the disclosure.
Figure 21:
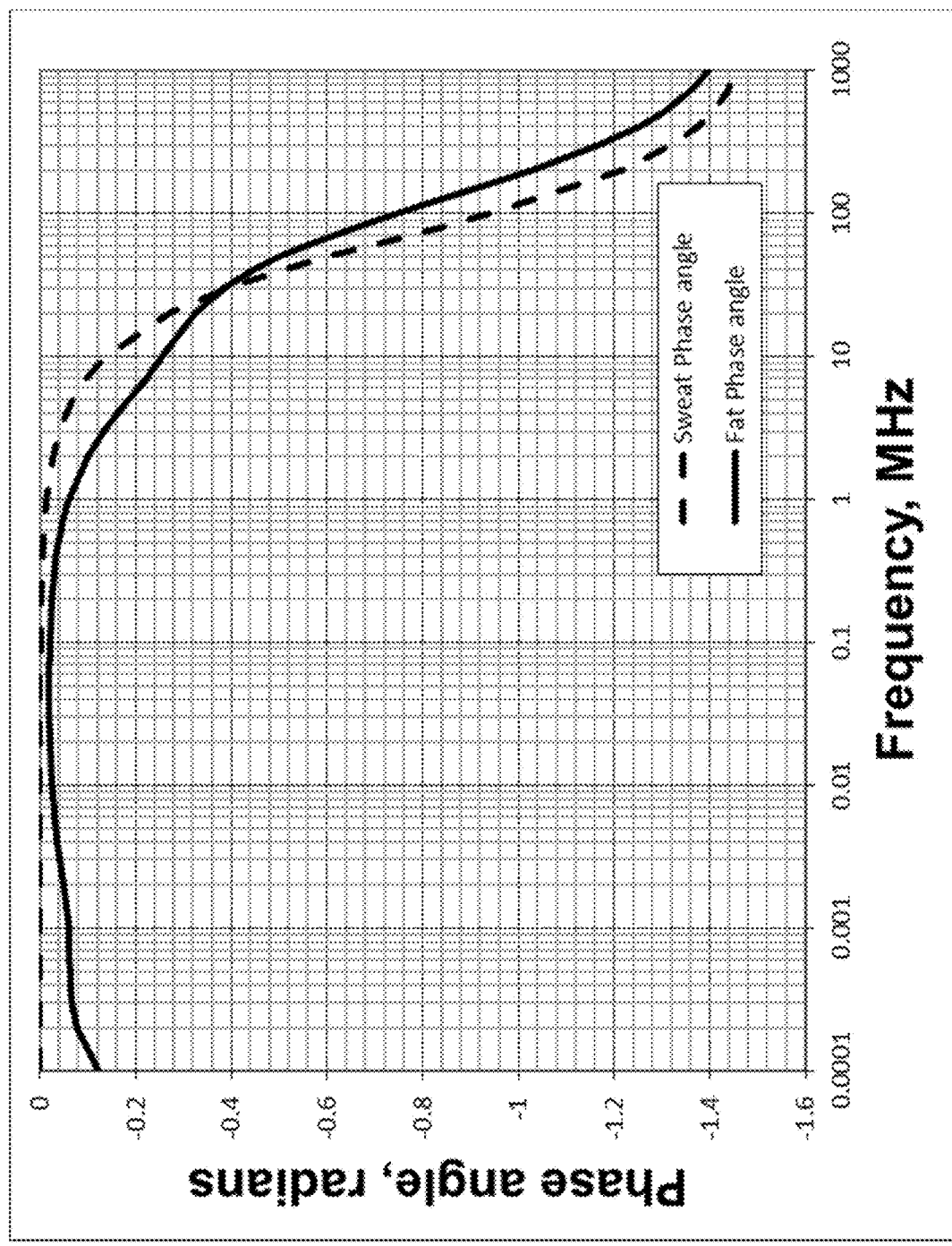
FIG. 21 is a plot showing phase angle of sweat versus fat as two different curves over a frequency range from about 0.0001 MHz to about 1000 MHz (e.g., 100 Hz to 1 GHz) according to an illustrative embodiment of the disclosure.
Figure 22:
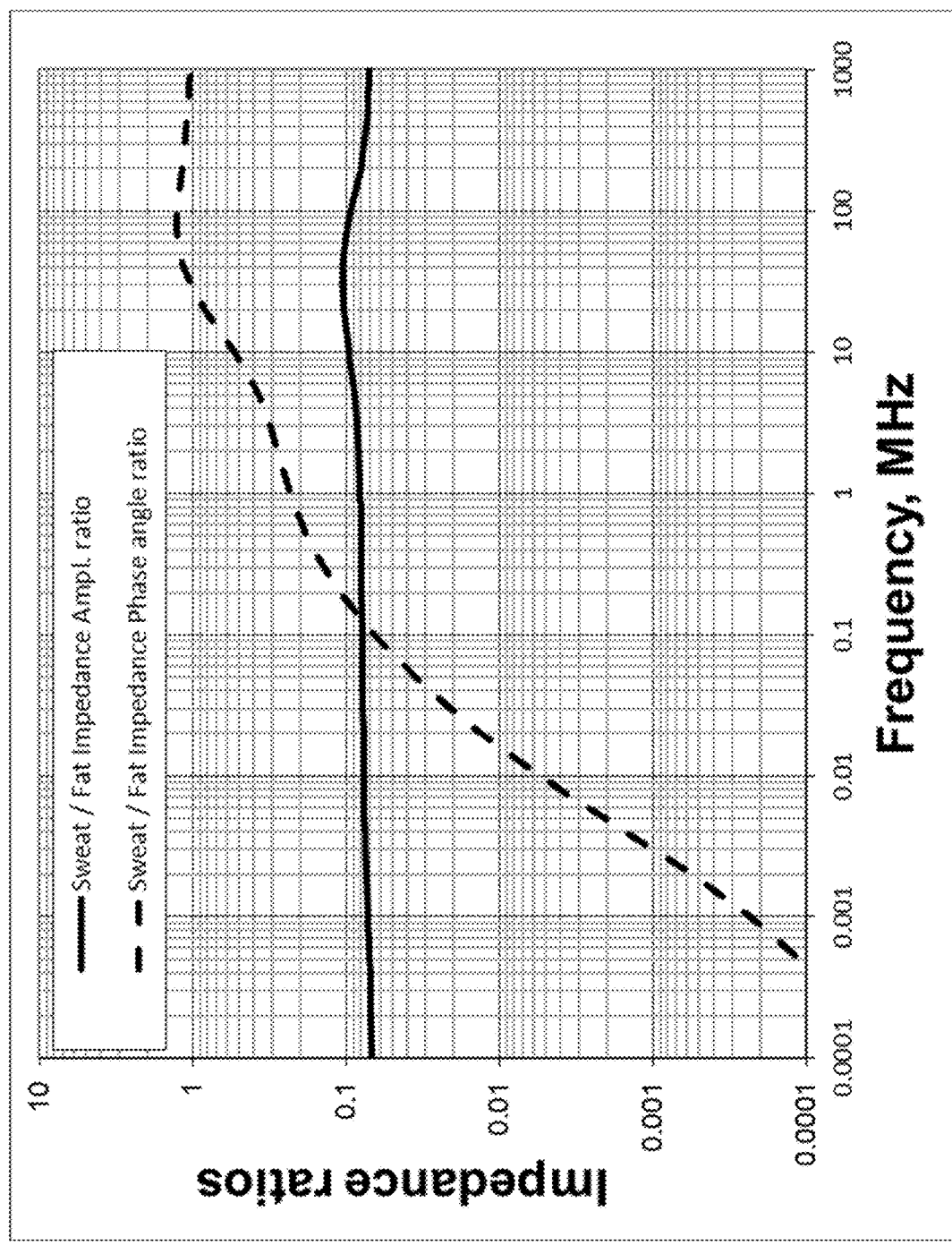
FIG. 22 is a plot showing impedance amplitude ratio and impedance phase angle ratio of sweat versus fat as two different curves over a frequency range from about 0.0001 MHz to about 1000 MHz (e.g., 100 Hz to 1 GHz) according to an illustrative embodiment of the disclosure.

FIG. 19 indicates that there are extensive frequency ranges where the dielectric properties of fat and sweat differ by a factor of more than about 2 or 5 or 10. The calculated specific electrical impedance amplitude |z| and phase angle θ for sweat and dermis are plotted on FIGS. 20 and 21 for frequencies between about 100 Hz and about 1 GHz. The ratios of the specific electrical impedance amplitude and phase angle of sweat vs fat are plotted on FIG. 22. FIG. 22 indicates that for frequencies between about 100 Hz and about 1 GHz the specific impedance amplitude of sweat is approximately about 10 times lower than the fat impedance. Delivery of RF power in the range between about 100 Hz and about 1 GHz through the electrodes identified to be in close proximity to targeted sweat gland will lead to selective power delivery to the sweat gland with up to about 10 times lower power density delivered in the surrounding fat. The RF electrodes in close proximity to each sweat gland identified for treatment are energized for a period of time corresponding to its thermal relaxation time R. Rox Anderson "*Selective Photothermolysis: Precise Microsurgery by Selective Absorption of Pulsed Radiation, Science*", Vol. 220 pp. 524-528.

The applicators or handpieces disclosed herein and variations thereof may be combined with control circuitry to regulate and count the number of uses such that exceeding a treatment limit may be tracked and result in handpiece being directly or remotely deactivated by the supplier or a control system.

Systems and methods utilizing RF energy to treat a patient's skin (e.g., dermis and hypodermis) or other target tissue at a depth below a tissue surface with RF energy are described herein. In various aspects, the present teachings can provide a non-invasive, cooled (or uncooled) RF-based treatment to achieve one or more of sebaceous gland treatment, acne treatment, sweat gland treatment, blood vessel treatment, spider vein treatment, gland damage/deactivation, skin tightening (laxity improvement), cellulite treatment apparatus, treatment to remove unwanted hairs and unwanted vascular lesions by way of non-limiting examples.

Figure 23:
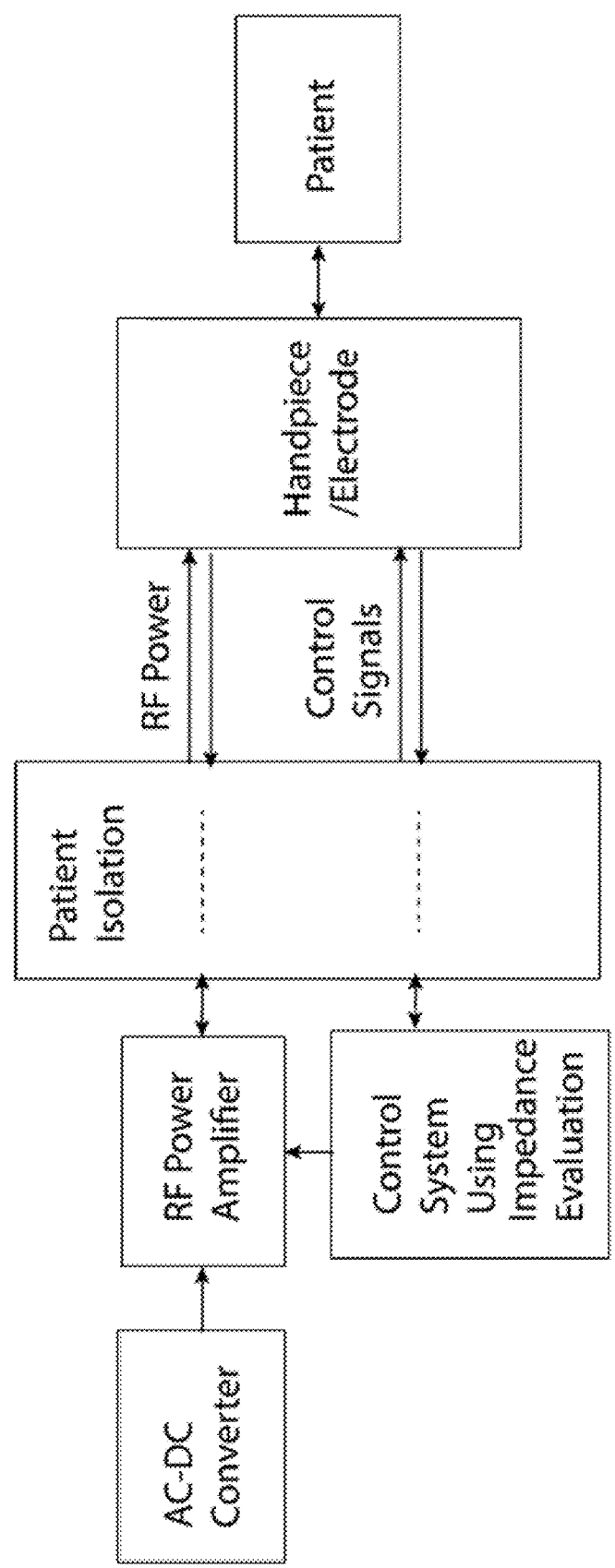
FIG. 23 schematically illustrates a block diagram of a temperature-controllable circuit topology for an RF-based system according to an illustrative embodiment of the disclosure.

FIG. 23 is a block diagram that shows the control system interacting with the impedance evaluation feedback around the pre-treatment diagnostic, pre-treatment impedance mapping, and treatment of a subject. Here, AC power is converted to DC voltage in the AC to DC converter. The DC voltage is delivered to the RF Power Amplifier and then travels through the Patient Isolation (e.g., a transformer). From Patient Isolation, the RF power is then delivered to the Handpiece/Electrode and the Electrode array (see, e.g., FIGS. 9 and 14) that is attached to the handpiece (e.g., FIG. 14) and then RF power is delivered to the Patient via the needles of the electrode array. The RF power may be delivered in monopolar mode or bipolar mode or the single system may be capable of delivering both monopolar mode and bipolar mode (e.g., the Potenza™ RF microneedling system manufactured by Jeisys Medical, Inc. combines monopolar and bipolar RF at 1 or 2 MHz in a single device). The Electrodes in the electrode array are also referred to as needles and microneedles. The RF power can be delivered to the Patient at a relatively low level suited for impedance diagnosis and/or impedance mapping and this RF power can range from about 1 nanoWatt to about 10 Watts. Alternatively, the RF power can be delivered to the Patient at a level suited for treating the condition of interest, e.g., acne, unwanted hair, excessive sweating, or unwanted vascular lesions (e.g., unwanted blood vessels). The RF power range for treatment ranges from about 1 milliwatt to about 10 Kilowatts, or from about 100 milliwatts to about 500 Watts.

Optionally, not shown in Figure A, the DC voltage travels through the DC Buck Converter, which controllably converts the supplied DC voltage to the desired RF frequency. The controlled DC voltage is delivered to the RF Power Amplifier and then travels through patient isolation (e.g., a transformer). From patient isolation, the RF power is then delivered to the Patient via the Handpiece/Electrode as disclosed herein.

Impedance Diagnostic/Impedance Mapping:

Referring still to FIG. 23, in order to accomplish Impedance Diagnostic/Impedance Mapping the relatively low-level RF power is delivered to the Patient via the Electrodes present on the Handpiece. The Control System provides Control Signals that instruct that low level RF power be multiplexed through the array of Electrodes present on the Handpiece to the Patient tissue being Diagnosed/Mapped. The Control System collects impedance information from the Patient tissue treatment area through received Control Signals that are employed to create Impedance Diagnostic information or an Impedance Map.

For example, when the RF power is delivered to the Patient at a relatively low level suited for impedance diagnosis and/or impedance mapping the RF power ranges from about 1 nanoWatt to about 10 Watts and a diagnostic scan of the tissue area is accomplished such the impedance of each electrode or alternatively the impedance between each pair of electrodes is measured using the Control Signals collected by the Control System.

The impedance value is determined for most if not all of the electrodes or pairs of electrodes within the array of the handpiece. The relative accuracy of the impedance map will be improved if more electrodes or pairs of electrodes are interrogated. The high and/or low impedance values from this diagnostic measurement may be excluded before a baseline impedance is established for this specific tissue area. In one embodiment, when an impedance value is determined to be high and/or low then the microneedle or the pair of microneedles associated with that high and/or low value is earmarked for subsequent therapeutic treatment depending on the treatment indication of interest. In another embodiment, once the baseline impedance is determined, the system will subsequently revisit the high and/or low impedance values and determine which ones to interrogate for therapeutic purposes based, for example, on the underlying frequency of the system.

Therapeutic Treatment:

Referring still to FIG. 23, based upon the impedance mapping of the patient tissue, a single electrode or a select subset of single electrodes on the handpiece (in monopolar mode) or a subset of pairs of electrodes on the handpiece (in bipolar mode) are energized to therapeutically treat the area identified as benefitting from the desired treatment as indicated by the impedance mapping of the patient tissue. In order to accomplish the therapeutic treatment RF power is delivered to the Patient via the Electrodes present on the Handpiece. The Control System provides Control Signals that instruct that RF power be multiplexed through the array of Electrodes present on the Handpiece to the Patient tissue that has been previously Impedance Mapped. The Control System multiplexes through single electrodes (in monopolar mode) or certain pairs of electrodes on the handpiece (in bipolar mode) based on the Impedance Map previously constructed using impedance data gathered from the region of Patient tissue being treated. For example, the RF power is delivered to the Patient at a level suited for treating the condition of interest, e.g., acne, unwanted hair, excessive sweating, or unwanted blood vessels. The RF power range for treatment ranges from about 1 milliwatt to about 10 Kilowatts, or from about 100 milliwatts to about 500 Watts.

Acne:

In one embodiment, a selected subset of pairs of adjacent needles or electrodes, are energized to therapeutically treat an enlarged sebaceous gland (ESGs) with RF energy. Impedance Mapping can be employed to identify the ESGs with relatively large diameter or largest diameter and then these mapped ESGs are treated using an RF power range and time suited for treatment. Impedance Mapping can also be employed to identify the ESGs with the highest lipid concentration between a pair of electrodes and then these mapped ESGs are treated using an RF power range and time suited for treatment. A relatively large ESG will make the space between pairs of needles appear to have a relatively high lipid concentration. Specifically, these needle pairs (in bipolar mode) may be energized for a time interval approximately equal to the thermal relaxation time of the tissue between each respective needle pair. Where a single needle (or a subset of single needles) makes direct contact with an ESG (in monopolar mode) each single needle may be energized for a time interval approximately equal to the thermal relaxation time of tissue in contact therewith. For some treatment sessions, whether a needle pair (in bipolar mode) or a single needle (in monopolar mode) selective RF heating will require high power for a short time.

Excessive Sweating:

In one embodiment, a selected subset of pairs of adjacent needles or electrodes, are energized to therapeutically treat sweat glands with RF energy. Impedance Mapping can be employed to identify the presence of sweat glands and then a selected subset of these mapped sweat glands are treated using an RF power range and time suited for treatment. Specifically, these needle pairs (in bipolar mode) may be energized for a time interval approximately equal to the thermal relaxation time of the tissue between each respective needle pair. For some treatment sessions, selective RF heating will require high power for a short time. In one embodiment, all sweat glands identified as present in a patient tissue area are treated using an RF power range and time suited for treatment.

Unwanted Hair Removal:

In one embodiment, a selected subset of pairs of adjacent needles or electrodes, are energized to therapeutically treat unwanted hair follicles with RF energy. Impedance Mapping can be employed to identify the presence of a hair shaft within a hair follicle and then a selected subset of these mapped hair follicles are treated using an RF power range and time suited for hair removal treatment. Specifically, these needle pairs (in bipolar mode) may be energized for a time interval approximately equal to the thermal relaxation time of the tissue between each respective needle pair. For some treatment sessions, selective RF heating will require high power for a short time. In one embodiment, all unwanted hair follicles identified as present in a patient tissue area are treated using an RF power range and time suited for treatment.

Unwanted Blood Vessels:

In one embodiment, a selected subset of pairs of adjacent needles or electrodes, are energized to therapeutically treat an unwanted blood vessel with RF energy. Impedance Mapping can be employed to identify the unwanted blood vessels by the elevated blood volume fraction and then these mapped unwanted blood vessels are treated using an RF power range and time suited for treatment. Alternatively, Impedance Mapping can be employed to identify the unwanted blood vessels by the enlarged blood vessels fraction and then these mapped unwanted blood vessels are treated using an RF power range and time suited for treatment. Specifically, these needle pairs (in bipolar mode) may be energized for a time interval approximately equal to the thermal relaxation time of the tissue between each respective needle pair. Where a single needle (or a subset of single needles) makes direct contact with an unwanted blood vessel (in monopolar mode) each single needle may be energized for a time interval approximately equal to the thermal relaxation time of tissue in contact therewith. For some treatment sessions, whether a needle pair (in bipolar mode) or a single needle (in monopolar mode) selective RF heating will require high power for a short time.

In general, the methods and systems disclosed herein may be used to provide various non-medical treatments such as cosmetic treatments, aesthetic treatments, and combinations thereof. Cosmetic treatment of tissue to reduce or prevent excess sweating, removal of unwanted hair, removal of blood vessels and lesions, reducing or preventing acne are all beneficial cosmetic treatments. These and other cosmetic treatments disclosed herein can improve the appearance and well being of those that suffer with the foregoing conditions and others disclosed herein. In various embodiment, the disclosure relates to methods of controlling transmission of RF energy such that one or more tissue targets are cosmetically treated to reduce, prevent, reverse, or otherwise cosmetically treat one or more of the unwanted conditions disclosed herein.

Additional details relating to various systems for using RF and impedance sensing to treat tissue are disclosed in U.S. Publication No. 20200352633 entitled "NON-INVASIVE, UNIFORM AND NON-UNIFORM RF METHODS AND SYSTEMS RELATED APPLICATIONS", the entire disclosure of which is hereby incorporated by reference in its entirety.

Further, additional details relating to various systems for using RF and impedance sensing to treat tissue are disclosed in U.S. Publication No. 20190239939 entitled "METHODS AND APPARATUS FOR CONTROLLED RF TREATMENTS AND RF GENERATOR SYSTEM", the entire disclosure of which is hereby incorporated by reference in its entirety.

It will be appreciated that for clarity, the following discussion will explicate various aspects of embodiments of the applicant's teachings, while omitting certain specific details wherever convenient or appropriate to do so. For example, discussion of like or analogous features in alternative embodiments may be somewhat abbreviated. Well-known ideas or concepts may also for brevity not be discussed in any great detail. The skilled person will recognize that some embodiments of the applicant's teachings may not require certain of the specifically described details in every implementation, which are set forth herein only to provide a thorough understanding of the embodiments. Similarly, it will be apparent that the described embodiments may be susceptible to alteration or variation according to common general knowledge without departing from the scope of the disclosure. The following detailed description of embodiments is not to be regarded as limiting the scope of the applicant's teachings in any manner.

The terms "about" and "substantially identical" as used herein, refer to variations in a numerical quantity that can occur, for example, through measuring or handling procedures in the real world; through inadvertent error in these procedures; through differences/faults in the manufacture of electrical elements; through electrical losses; as well as variations that would be recognized by one skilled in the art as being equivalent so long as such variations do not encompass known values practiced by the prior art. Typically, the term "about" means greater or lesser than the value or range of values stated by $\frac{1}{10}$ of the stated value, e.g., ±10%. For instance, applying a voltage of about +3V DC to an element can mean a voltage between +2.7V DC and +3.3V DC. Likewise, wherein values are said to be "substantially identical," the values may differ by up to 5%. Whether or not modified by the term "about" or "substantially" identical, quantitative values recited in the claims include equivalents to the recited values, e.g., variations in the numerical quantity of such values that can occur, but would be recognized to be equivalents by a person skilled in the art.

Moreover, nothing disclosed herein is intended to be dedicated to the public regardless of whether such disclosure is explicitly recited in the claims. To aid the Patent Office and any readers of any patent issued on this application in interpreting the claims appended hereto or otherwise presented throughout prosecution of this or any continuing patent application, applicants wish to note that they do not intend any claimed feature to be construed under or otherwise to invoke the provisions of 35 USC 112(f), unless the phrase "means for" or "step for" is explicitly used in the particular claim.

All of the drawings submitted herewith include one or more ornamental features and views, each of which include solid lines any of which also incorporate and correspond to and provide support for dotted lines and alternatively, each of which include dotted lines any of which also incorporate and correspond to and provide support for solid lines.

The use of the terms "include," "includes," "including," "have," "has," or "having" should be generally understood as open-ended and non-limiting unless specifically stated otherwise.

The use of the singular herein includes the plural (and vice versa) unless specifically stated otherwise. Moreover, the singular forms "a," "an," and "the" include plural forms unless the context clearly dictates otherwise. In addition, where the use of the term "about" is before a quantitative value, the present teachings also include the specific quantitative value itself, unless specifically stated otherwise.

It should be understood that the order of steps or order for performing certain actions is immaterial so long as the present teachings remain operable. Moreover, two or more steps or actions may be conducted simultaneously.

Where a range or list of values is provided, each intervening value between the upper and lower limits of that range or list of values is individually contemplated and is encompassed within the disclosure as if each value were specifically enumerated herein. In addition, smaller ranges between and including the upper and lower limits of a given range are contemplated and encompassed within the disclosure. The listing of exemplary values or ranges is not a disclaimer of other values or ranges between and including the upper and lower limits of a given range.

It should be appreciated that numerous changes can be made to the disclosed embodiments without departing from the scope of the present teachings. While the foregoing figures and examples refer to specific elements, this is intended to be by way of example and illustration only and not by way of limitation. It should be appreciated by the person skilled in the art that various changes can be made in form and details to the disclosed embodiments without departing from the scope of the teachings encompassed by the appended claims.

The invention claimed is:

1. A method of treating acne, the method comprising:
   providing a needle array comprising a plurality of needles;
   inserting plurality of needles into a dermis of a treatment area;
   sending a low power pulse through each of the plurality of needles;
   collecting impedance data relative to each of the plurality of needles;
   detecting a location of an enlarged sebaceous gland in response to impedance data; and
   energizing one or more of the plurality of needles to thermally treat the enlarged sebaceous gland, wherein normally sized sebaceous glands are spared from targeted energy exposure in response to contrast between impedance data.

2. The method of claim 1, wherein an enlarged sebaceous gland has diameter greater than about 50 μm.

3. The method of claim 2, wherein the low power pulse is a series of low power pulses that are iteratively sent until the collected impedance data shows contrast indicating the presence or absence of enlarged sebaceous glands.

4. The method of claim 1, wherein energizing comprises:
   sending energy through a needle of the plurality of needles located near the enlarged sebaceous gland.

5. The method of claim 1, wherein one or more needles comprise liquid delivery ports and a channel to receive a solution.

6. The method of claim 5, wherein the solution is a conductive solution.

7. The method of claim 1 further comprising addressing one or more needles of the plurality of needles according to an energizing scheme such as a multiplexing sequence.

8. The method of claim 1, wherein the plurality of needles is arranged in hexagonal clusters of needles, wherein one needle is disposed within each such cluster.

9. The method of claim 1 wherein detecting a location of an enlarged sebaceous gland further comprises performing an impedance mapping relative to the treatment area.

10. The method of claim 9, wherein detecting a location of an enlarged sebaceous gland further comprises identifying the enlarged sebaceous gland in response to one or more impedance measurements obtained during the impedance mapping.

11. The method of claim 1, wherein detecting a location of an enlarged sebaceous gland further comprises measuring a difference in impedance between two adjacent needles spanning the sebaceous gland.

12. The method of claim 1 further comprising performing a diagnostic impedance measurement relative to the treatment area.

13. The method of claim 12 further comprising excluding high and/or low impedance values from the diagnostic measurement.

14. A method of cosmetically treating tissue, the method comprising:
   providing a needle array comprising a plurality of needles;
   inserting plurality of needles into on one or more tissue layers of a treatment area;
   sending a low power pulse through each of the plurality of needles;
   collecting impedance data relative to each of the plurality of needles;
   determining which of the plurality of needles is near the tissue target based on the collected impedance data;
   detecting a location of a tissue target using the collected impedance data, wherein the tissue target comprises an enlarged sebaceous gland;
   energizing one or more of the plurality of needles to cosmetically treat one or more portions of a the tissue target by selectively heating the one or more portions of the tissue target to cause thermal damage; and
   sparring one or more normal sebaceous glands based on contrast between collected impedance, the contrast between collected impedance data indicating the presence or absence of enlarged sebaceous glands.

15. The method of claim 14, wherein detecting a location of a tissue target further comprises measuring a difference in impedance between two adjacent needles spanning the tissue target.

16. The method of claim 14, wherein detecting a location of a target tissue further comprises performing an impedance mapping relative to the treatment area.

17. The method of claim 14 wherein the low power pulse comprises a series of low power pulses that are iteratively sent until the collected impedance data shows the contrast.

18. The method of claim 14, wherein the plurality of needles comprises one or more groups of seven needles, the needles arranged in a hexagonal pattern with one central needle and the other six needles symmetrically arranged around the central needle.

* * * * *